US012730107B2

(12) United States Patent
Liu et al.

(10) Patent No.: US 12,730,107 B2
(45) Date of Patent: Sep. 8, 2026

(54) REAGENT COMPOSITION FOR IMMUNOPHENOTYPING OF B LYMPHOBLASTIC LEUKEMIA/LYMPHOMA AND USE THEREOF

(71) Applicant: Peking University People's Hospital, Beijing (CN)

(72) Inventors: Yanrong Liu, Beijing (CN); Yazhe Wang, Beijing (CN)

(*) Notice: Subject to any disclaimer, the term of this patent is extended or adjusted under 35 U.S.C. 154(b) by 693 days.

(21) Appl. No.: 18/300,028

(22) Filed: Apr. 13, 2023

(65) Prior Publication Data

US 2023/0333110 A1 Oct. 19, 2023

(30) Foreign Application Priority Data

Apr. 13, 2022 (CN) ......................... 202210381388.9

(51) Int. Cl.
*G01N 33/57505* (2026.01)
*G01N 15/14* (2006.01)

(52) U.S. Cl.
CPC ....... *G01N 33/57505* (2026.01); *G01N 15/14* (2013.01); *G01N 2333/70503* (2013.01); *G01N 2800/7028* (2013.01)

(58) Field of Classification Search
CPC ..... G01N 33/57426; G01N 2800/7028; G01N 2015/1006; G01N 2015/1402;

(Continued)

(56) References Cited

U.S. PATENT DOCUMENTS

2007/0041981 A1 2/2007 Howard et al.
2012/0165213 A1 6/2012 Van Dongen et al.

FOREIGN PATENT DOCUMENTS

CN 103018463 A 4/2013
CN 113777327 A 12/2021
CN 114213540 A 3/2022

OTHER PUBLICATIONS

Chen, Man, et al. "One tube 24 color full spectral flow cytometry and multi-dimensional software to study the maturation pattern and antigen expression of the myeloid." Blood 136 (2020): 13-14. (Year: 2020).*

(Continued)

*Primary Examiner* — Bao-Thuy L Nguyen
*Assistant Examiner* — Christopher Evans

(57) ABSTRACT

Provided is a reagent composition for immunophenotyping and MRD monitoring of B lymphoblastic leukemia/lymphoma (B-ALL/LBL). The reagent composition includes a 20-antibody combination. In the present disclosure, the antibody combination, the fluorescent labeling combination for the corresponding antibody, and the result interpretation methods are optimized. It only needs to use 20 kinds of antibodies in a single tube of cells for one sample loading, allowing for comprehensively and efficiently performing subtype typing on B lymphoblastic leukemia/lymphoma. In addition, it enables to predict part of recurrent genetically abnormal B-ALL/LBL and has high sensitivity and specificity for the diagnosis of the subtype of BCR/ABL1 gene. Meanwhile, it enables to determine the leukemia-related immunophenotype (LAIP) for minimal residual disease (MRD) monitoring after treatment by using the combination and used for MRD monitoring and CAR-T post-treatment monitoring.

6 Claims, 16 Drawing Sheets

(58) Field of Classification Search
CPC ..... G01N 2015/1488; G01N 33/57484; G01N 33/582; G01N 33/56972; G01N 33/57505
See application file for complete search history.

(56) References Cited

OTHER PUBLICATIONS

Van Dongen, J. J. M., et al. "EuroFlow antibody panels for standardized n-dimensional flow cytometric immunophenotyping of normal, reactive and malignant leukocytes." Leukemia 26.9 (2012): 1908-1975. (Year: 2012).*

"Cytek Aurora Fluorochrome Selection Guidelines 3 Laser 16V 14B 8R" Cytek. Published Oct. 21, 2019 (Year: 2019).*

"Acquisition Protocol for Cytek 25-Color Immunoprofiling Assay" Cytek. Published Sep. 28, 2021 (Year: 2021).*

Zhang, "The Role of Flow Cytometry in the Diagnosis and Treatment of B Cell Lymphoma," Anti-tumor Pharmacy, vol. 2, No. 5, Oct. 2012, pp. 322-331, including English abstract.

Xue et al., "Progression of children with minimal residual disease of positive B lineage acute lymphocytic leukemia," J Clin Pediatr, vol. 25, No. 8, Aug. 2007, pp. 636-643, including English abstract.

Wang, "Clinical application of immunophenotyping in acute leukemia," Chongqing Medicine, vol. 37, Issue 20, Oct. 2008, 9 pages (including 6 pages English Translation).

* cited by examiner

REAGENT COMPOSITION FOR IMMUNOPHENOTYPING OF B LYMPHOBLASTIC LEUKEMIA/LYMPHOMA AND USE THEREOF

CROSS-REFERENCE TO RELATED APPLICATION

This patent application claims the benefit and priority of Chinese Patent Application No. CN202210381388.9, entitled "Reagent Composition for Immunophenotyping of B Lymphoblastic Leukemia/Lymphoma and Use Thereof", filed with the China National Intellectual Property Administration on Apr. 13, 2022, the disclosure of which is incorporated by reference herein in its entirety as part of the present application.

TECHNICAL FIELD

The present disclosure relates to the field of antibody therapeutics, in particular to a group of reagent compositions for immunophenotyping of B lymphoblastic leukemia/lymphoma and use thereof.

BACKGROUND

Lymphoblastic leukemia/lymphoma (ALL/LBL) is a kind of malignant tumor originating from the lymphocyte precursor. This disease can involve the bone marrow and peripheral blood (ALL) and can also involve lymph nodes, thymus, or extranodal tissue (LBL). Usually, when the lesion is mainly present in the form of a mass and does not involve peripheral blood or bone marrow, it would be more appropriate to be diagnosed as LBL, and when it is manifested mainly by a large number of blast cells detected in PB or BM, it would be more appropriate to be diagnosed as ALL. ALL/LBL can be divided into two categories by using immunological methods: B cells and T cells. The clinical manifestations, treatment options, and prognosis of the two types of diseases are different, and their accurate diagnosis and classification are of important clinical value.

The classification of B lymphoblastic leukemia/lymphoma (B-ALL/LBL) according to the WHO classification of tumors of hematopoietic and lymphoid tissues (2017) is shown in Table 1, which is categorized into 2 categories: B-ALL/LBL not otherwise specified (NOS) and B-ALL/LBL with recurrent genetic abnormalities. Through immunophenotyping, B-ALL/LBL NOS can be divided into three subtypes: Pro, Common, and Pre. In B-ALL/LBL with recurrent genetic abnormalities, 4 types (see Table 2) show certain immunophenotype characteristics. Immunophenotyping is somewhat indicative of genotyping, but the diagnosis requires genetic and chromosomal diagnosis. Other genotyping and immunophenotyping are not predictive.

TABLE 1

| WHO classification of B lymphoblastic leukemia/lymphoma (B-ALL/LBL) (2017) |
|---|
| B lymphoblastic leukemia/lymphoma (B-ALL/LBL), not otherwise specified (NOS) |
| Pro-B-ALL |
| Common-B-ALL |
| Pre-B-ALL |
| B-ALL/LBL with recurrent genetic abnormalities |
| B-ALL/LBL with t (9; 22) (q34; q11.2); BCR-ABL1 |
| B-ALL/LBL with t (v; 11q23.3); KMT2A rearrangement |
| B-ALL/LBL with t (12; 21) (p13.2; q22.1); ETV6-RUNX1 |
| B-ALL/LBL with hyperdiploidy |
| B-ALL/LBL with hypodiploidy |
| B-ALL/LBL with t (5; 14) (q31.1; q32.3); IL3-IGH |
| B-ALL/LBL with t (1; 19) (q23; p13.3); TCF-PBX1 |
| Temporary classification: B-ALL/LBL BCR-ABL1-Like |
| B-ALL/LBL with iAMP21 |

TABLE 2

Immunophenotyping characteristics of B-ALL/LBL with genetic abnormalities

| B-ALL/LBL with | Immunophenotype characteristics |
|---|---|
| t (9; 22) (q34; q11.2); BCR-ABL1 | $CD19^{+}CD10^{+}TdT^{+}CD34^{st+}CD38^{dim}$, more expressed CD13, CD33, CD66c and CD25, not CD117 |
| t (v; 11q23.3); KMT2A rearrangement | Common in Pro-B-ALL, $CD19^{+}CD10^{-}$CD24; CD15 and/or CD65 commonly expressed, and NG2 specifically expressed |
| T (12; 21) (p13.2; q22.1); ETV6-RUNX1 | More common in Common-B-ALL, $CD19^{+}CD10^{+}CD34^{+}$, and almost no expression of CD9, CD20, CD66c |
| t(1; 19) (q23; p13.3); TCF-PBX1 | More common in Pre-B-ALL, $CD19^{+}CD10^{+}$ $c\mu^{+}$. In the case of $c\mu^{+}$, blast cells strongly express CD9 and CD34 is negative. |

The following goals can be achieved by immunophenotyping B-ALL/LBL through FCM:

The first goal: determine whether it is B-ALL/LBL. The second goal: determine the subtype. The third goal is to look for leukemia-associated immunophenotype (LAIP) that is the marker for testing the minimal residual disease (MRD) in the next step. The fourth goal: screen for markers associated with treatment targets are expressed. The fifth goal is to help judge a specific genotype, as shown in Table 2.

Different B-ALL/LBLs have different biological characteristics and have different curative effects in clinical treatment. Therefore, accurate diagnosis is the basis for choosing appropriate treatment. Among them, genetic abnormalities have a great impact on prognosis. For example, B-ALL/LBL with t (9;22) (q34;q11.2), also known as $Ph^{+}$ALL, has the highest incidence rate in adult B-ALL/LBL with recurrent genetic abnormalities. This type of leukemia has always been a type of disease with a very poor prognosis. Only hematopoietic stem cell transplantation can result in possible long-term survival. However, with the emergence of specific targeted drug-tyrosine kinase inhibitors, its curative effect has been significantly improved, and the long-term survival rate has been greatly improved. Therefore, the diagnosis of this type of special genetically abnormal leukemia is particularly important. If a rapid immunophenotyping test allows for preliminary prediction of $Ph^{+}$ALL and indicates the doctor to complete the gene and genetic testing of the patient, then it will play a vital role in choosing the correct therapy for the patient.

Despite improvements in the treatment of acute lymphoblastic leukemia have been in the past few decades, the 5-year disease-free survival rate in adults remains low, ranging from 10% to 20%. Disease in more than 20% of patients will relapse, after which few treatment options are available. Chimeric antigen receptor T-cell therapy (CAR-T) is a better treatment method that emerges in recent years. Particularly, anti-CD19-CAR-T therapy is effective and safe for patients with refractory/recurrent B cells acute lymphoblastic leukemia. At present, CD22-CAR-T is still being used clinically, and even dual CAR-T of CD19-CD22 against 2 antigens. Following these CAR-T treatments, CD19 or CD22 antigen-negative relapse may occur, which seriously affects the recognition of B cells. It is necessary to select antigens other than CD19 and CD22 to recognize B cells and to detect the phenotype and proportion of leukemia B cells.

With the deepening of research and the development of new target drugs, more antibodies need to be detected, the types of antibodies that need to be detected before treatment increase accordingly, which have reached about 20-30 kinds of antibodies. However, the commonly used detection method of flow cytometry in current clinical practice involves a four-color- or eight-to-ten-color antibody combination (Chinese expert consensus on four-color flow cytometry for immunophenotyping of acute leukemia. Chinese Hematology, Clinical Flow Cytometry Group, Blood Immunology Division, Chinese Society of Immunology Journal, 2015, vol. 36, No. 4,265-271). Therefore, it is necessary to design a multi-tube combination. The expert consensus in 2015 recommended testing 19 antibodies for B-ALL/LBL in a total of 5 tubes. However, these antibodies can no longer meet clinical needs.

The problem with the current detection method is that several tubes of cells need to be labeled at the same time to complete the detection of about 20 kinds of antibodies. To facilitate the analysis of the phenotype of a certain cell in different tubes, more gating antibodies need to be used repeatedly, resulting in a larger total number of antibodies to be detected and high costs. If the number of repeated gating antibodies is reduced, it will be difficult to accurately analyze the relationship between the detected antibodies in different tubes, which will affect the judgment of cell lineage, differentiation stages, and benign and malignant cells. In addition, since several tubes of antibody combination are required to complete the test, and the types of antibody, the clone number, and the fluorescein selected for each tube are different, these will substantially affect the results of antibody testing. Therefore, it is necessary to optimize antibody design from a domestic and international view and establish a unified antibody combination to ensure the consistency and accuracy of the test results.

The emergence of new FCM and new fluorescein provides more space for the development of flow cytometry, making it possible to detect more antibodies in one tube. By using current clinical instruments, it is possible to detect more than 20 kinds of antibodies simultaneously, which provides favorable conditions for designing 1-2 tubes of multiple antibody combinations. But the difficulty it faces is that there are more than 50 kinds of fluorescein available for selection, and each fluorescein has a different excitation spectrum, emission spectrum, and different fluorescence brightness (represented by stain index). During the matching of the flow cytometric fluorescein, especially when there are more than 20 colors, researchers need to fully consider the similarity between different fluorescein, the spillover performance, the stain index, the complexity index of multicolor schemes, and the differences in antigen expression. In particular, the design of the protocol can only be completed by comprehensively considering factors such as the co-expression of different labeled antigens. However, antigen expression can become stronger, weaker, or even absent after the malignant transformation of cells. In addition, there are differences in the quality and types of antibodies commercialized by different manufacturers and the types of fluorescein available for selection. Even for the same kind of fluorescein, the fluorescence intensity of products from different manufacturers may be different. Moreover, not all antibodies produced by the same well-known brand manufacturer are of good quality. These factors complicate the matching of antibody colors. Therefore, even if the scheme is obtained by combining the above factors, it still needs repeated tests on real patient samples and multiple adjustments based on the test results to obtain a detection scheme that finally performs well in such samples. This requires researchers to have a wealth of knowledge in aspects such as blood diseases, cellular immune labeling, fluorescein and flow cytometry to arrive at the scheme. On the other hand, since the multi-color technical solution based on spectral flow is different from traditional flow methods, there are stricter requirements for the single-tube multi-color technical solution, and such a combination of solutions can provide more diverse and comprehensive detection information following one attempt of sample loading, which cannot be achieved by conventional flow cytometry detection methods. These factors determine that for a certain disease, instead of merely knowing which antibodies need to be detected and an arbitrary selection of a species of fluorescein allows for forming a combination of schemes that can be used for clinical detection. This is a creative project. Currently, there have no reports that a combination of 20 antibodies is used for clinical immunophenotyping of B-acute lymphoblastic leukemia/lymphoma.

To solve the problems existing in the current conventional flow cytometry methods, improve the ability to identify tumor cells, improve detection efficiency, and reduce the economic burden of patients, it is necessary to design a new antibody combination to reduce the number of detection tubes and increase the number of antibodies to be detected in each tube to improve the accuracy of analysis and clinical detection level. Aiming at these problems, this application was proposed, and its clinical applicability has been verified. The results proved that compared with the conventional 10-color antibody combination in clinical practice, the 20 antibodies designed in the present disclosure and the selected fluorescein allow for achieving the inspection in a 4-tube combination, enabling accurate detection of B lymphoblastic leukemia/lymphoma Immunophenotyping. Meanwhile, the 20-color combination is better than the 10-color combination, and the CD20-efluor450 produces stronger signals than the CD20 APC-Cy7 in the 10-color combination, which makes the predictive positive rate of $Ph^+$ALL significantly higher than that in the 10-color combination. In addition, the newly added CD21 and CD25 antibodies, combined with CD66, CD13, and CD38, provided predictive sensitivity of 92.86% and specificity of 90.0% for $Ph^+$ALL, respectively, and the positive predictive value and negative predictive value were 81.25% and 96.42%, which were significantly better than the conventional 10-color method, providing important clues for doctors to choose correct detection and therapies. The 10-color antibody combination predicts the sensitivity and specificity of $Ph^+$ALL to be 50% and 75%, respectively (Table 7), and the positive predictive value and negative predictive value are 50% and 75%, respectively. It is less practical.

B-ALL/LBL with t (v;11q23.3); KMT2A rearrangement can be predicted successfully. B-ALL/LBL with t (12;21) (p13.2;q22.1);ETV6-RUNX1, the phenotype is consistent with that reported in the literature.

In addition, since this combination allows for detecting 20 kinds of antibodies simultaneously, it is possible to gate the B cells by binding CD24 to CD38, CD45, CD15, or SSC following the treatment with CD19-CAR-T or CD22-CAR-T. Furthermore, by combining other antibodies such as HLA-DR, CD81, and CD123 in this combination, all of these markers can be used together for the recognition of tumor B cells, the combination of the present disclosure can be used for detecting immunophenotype and monitoring minimal residual leukemia (MRD) following treatment with CD19-CAR-T or CD22-CAR-T, with a detection effect achieved with one tube rather than 3-4 tubes in the past. Besides, the need for labeling cytoplasmic antibodies is eliminated, thereby reducing operation steps and instability of results, meeting the clinical need for MRD detection after CD19-CAR-T or CD22-CAR-T therapy for all B lymphoblastic leukemia/lymphoma.

The technical solution in the present disclosure will help improve the standardization and consistency of detection and improve the clinical detection level for immunophenotyping and MRD.

SUMMARY

In order to solve the above problems, the purpose of the present disclosure is to provide an antibody composition for immunophenotyping of B lymphoblastic leukemia/lymphoma (B-ALL/LBL). Specifically, the composition comprises 20 antibodies, which are mainly for typing of B-ALL/LBL subtypes, screening of markers for minimal residual disease (MRD) and therapeutic target, prediction of genotyping, and MRD monitoring to achieve comprehensive immunophenotyping of B-ALL/LBL.

Primary screening of blood tumors (the first step of detection) is conducted by using a tube of 19-antibody combination described in the patent application No. CN2021110670743, and the blood tumors are categorized into 9 classes: AML, ALL-T, ALL-B, MPAL, NHL-B, NHL-T, NHL-NK, PCN, and chronic myeloid diseases, and a clear diagnosis was made for 7 categories of tumors, AML, ALL-T, ALL-B, MPAL, NHL-B, NHL-T, and PCN. The specimens identified as ALL-B was combined with one tube containing 20 antibodies of this application (the second step of detection), and a total of 2 tubes of antibody combination allows for comprehensive immunophenotyping and subtype typing of B-ALL/LBL. In this application, screening for B-ALL/LBL MRD markers and therapeutic target as well as prediction of genotyping and MRD monitoring can be performed by using one single tube.

In order to achieve the above purpose, the present disclosure provides the following specific technical solution.

In a first aspect, the present disclosure provides a reagent composition for use in immunophenotyping and/or MRD monitoring of B-ALL/LBL, comprising 20 kinds of antibodies.

Preferably, the antibody types and compatible fluorescein of the reagent composition are shown in Table 3.

TABLE 3

B-ALL/LBL antibody combination information and expressing cells used in the present disclosure

| Antigen | Clone number | Fluorescein | Expressing cells |
|---|---|---|---|
| CD22 | 4KB128 | SB436 | Pan B cells have the strongest expression in the mature stage. |
| CD20 | 2H7 | eFluor450 | Mid-differentiation stage and mature B cells, partially T cells |
| CD21 | B-ly4 | BV480 | Mature B cells, FDC, T subpopulations |
| CD45 | HI30 | BV510 | Used to group white blood cells, immature cells usually weakly express. |
| CD10 | HI10A | BV605 | Neutrophilic segmented granulocytes, early B cells |
| CD19 | SJ25C1 | BV650 | Pan B cells, normal plasma cells |
| CD24 | ML5 | BV711 | B cells, granulocytes, epithelial cells, monocytes, and T subpopulation cells |
| CD123 | 6H6 | BV785 | Eosinophils/basophils and PDC, precursor myeloid cells, mastocytes, megakaryocytes, a small portion of lymphocytes |
| CD65 | B36299 | FITC | Granulocytes, partially monocytes, myeloid white blood cells |

TABLE 3-continued

| B-ALL/LBL antibody combination information and expressing cells used in the present disclosure | | | |
|---|---|---|---|
| Antigen | Clone number | Fluorescein | Expressing cells |
| CD15 | HI98 | cFluorB548 | Promyelocytes to mature granulocytes, monocytes, and eosinophilic granulocytes |
| CD13 | L138 | PE | Granulocytes and monocytes, myeloid progenitor cells, endothelial cells, epithelial cells, and dendritic cells (DC) |
| lambda | MHL-38 | PE-Dazzle594 | Mature B cells, plasma cells, restrictively expressed as a clonal marker |
| HLA-DR | G46.6 | PE-Cy5 | Early granulocytes and mature monocytes, B cells, activated T cells |
| CD34 | 581 | PerCP-Cy5.5 | T cells, B cells, immature myeloid cells, HSC, endothelial cells |
| CD58 | TS2/9 | PerCP-Vio700 | White blood cells, red blood cells, epithelial cells, endothelial cells, fibrocytes |
| CD81 | 5A6 | PE-Cy7 | T cells, B cells, NK cells, monocytes, dendritic cells (DC), endothelial cells |
| CD66a/c/e | ASL-32 | AF647 | Granulocytes, epithelial cells, colon cells |
| Kappa | MHK-49 | eFluorR720 | Mature B cells, plasma cells, restrictively expressed as a clonal marker |
| CD38 | HB-7 | APC-Fire750 | Immature myeloid cells and mature monocytes, early B cells, activated T cells, and plasma cells express strongly |
| CD25 | M-A251 | APC-Fire810 | Activated T/B cells, monocytes, dendritic cell (DC) subpopulation, Treg cells |

Preferably, all the antibodies are monoclonal antibodies.

In a second aspect, the present disclosure provides a kit for immunophenotyping B lymphoblastic leukemia/lymphoma and/or monitoring MRD, the kit comprises the reagent composition and compatible fluorescein.

Preferably, the kit also comprises red blood cell lysate and buffer.

In a third aspect, the present disclosure provides a system for detecting B lymphoblastic leukemia/lymphoma immunophenotyping and/or MRD detection, and the system includes a detection part and an analysis part, wherein:

the detection part is used to detect a reagent of a sample to be tested in one-tube flow cytometry to obtain a test result of the sample, wherein the reagent comprises the reagent composition in any item as described above;

the analysis part is used to analyze the test results from the detection part.

Preferably, the system is used to detect an immunophenotype of B lymphoblastic leukemia/lymphoma and to monitor MRD, comprising the following steps:

preparing a flow cytometric sample by Using the reagent composition after treating a sample to be tested, performing flow cytometric detection;

wherein gating is performed according to the following steps when the flow cytometry is performed:

setting a living cell gate R1, excluding debris and dead cells; setting a lymphocyte gate, a monocyte gate, a granulocyte gate, a nucleated red blood cell gate, and an immature cell gate within gate R1 using CD45/SSC; wherein the immature cells in B lymphoblastic leukemia/lymphoma are immature B cells; when it is not favorable to set a gate for immature B cells in CD45/SSC plot, it will be favorable to set a gate for $CD19^{+}$ B cells using CD45/CD19 or SSC/CD19, and the latter gating method is used for MRD monitoring;

analyzing the immunophenotype of immune B cells.

In a fourth aspect, the present disclosure provides the use of the reagent composition, the kit, or the system described in the preparation of a product for immunophenotyping B lymphoblastic leukemia/lymphoma, screening for a target in target therapy, and screening for a marker for monitoring minimal residual disease, and for monitoring minimal residual disease.

Further, B lymphoblastic leukemia/lymphoma includes 1. B-ALL/LBL non-specific type (NOS); 2 and B-ALL/LBL with recurrent genetic abnormalities.

The reagent composition described in the present disclosure is used for screening of MRD markers in B-ALL/LBL, for typing of type 1 B-ALL/LBL subtype, and genotyping prediction of reproducible genetic for some B-ALL/LBL aberrations.

In a fifth aspect, the present disclosure further provides a method for predicting BCR/ABL1 gene subtype, including conducting integration for 6 markers of CD20, CD21, $CD38^{dim}$, CD66, CD25, and CD13, each antigen positive is assigned as 1 point, a score of ≥3 is predicted as $BCR/ABL1^{+}$, and a score of <3 is predicted as $BCR/ABL1^{-}$.

In a sixth aspect, because the relapse of CD19 or CD22 negative following CD19-CAR-T or CD22-CAR-T treatment, the present disclosure provides a method for detecting immune B cells by gating and analyzing CD24 and/or CD38, which is used for immunophenotyping and MRD monitoring following treatment with CD19-CAR-T or CD22-CAR-T in In t (v;11q23.3);KMT2A gene positive and negative patients with B-ALL/LBL, with the advantages of elimination of the need for cytoplasmic antibody, shortened operation link, time-saving, and avoidance of false negatives caused by cytoplasmic antibody labeling.

Based on the above technical solutions, the present disclosure has the following beneficial effects.

Use of a set of 20-antibody combinations enables the immunophenotyping of B lymphoblastic leukemia/lymphoma. When used together with primary screening tubes for hematological tumors, only 2 tubes of antibody combination are needed for comprehensive typing of B-ALL/LBL, with the effect being much better than that of a 4-color combination and a 8-color combination. At present, 8-10 color antibody combinations are commonly used clinically, and 3 to 4 tubes of antibody combinations are required for the testing of B-ALL/LBL. In the present disclosure, one (1) single tube of antibody combination is used, which reduces the demand for specimens and the number of operation steps, reduces labor intensity, and saves operational time consumption. Meanwhile, repeated application of gating antibodies is reduced, the number of effective antibodies is increased, and the relationship between the mutual expression of 20 antibodies can be observed simultaneously, for example, simultaneous expression of antibodies, while in the prior art analysis, only 8-10 antibodies can be detected whether they are expressed at the same time. Therefore, in the present disclosure, the analysis ability is greatly improved. This powerful analysis ability enables to increase the accuracy of analysis and the ability to identify tumor cells, improve the accuracy of diagnosis, and increase the specificity and sensitivity of detection. The technical solutions in the present disclosure ensure accurate diagnosis and precise classification of B-ALL/LBL and provide a basis for selecting appropriate therapy. Using this antibody combination, a scoring method for predicting B-ALL/LBL with BCR/ABL1 gene subtype is established, which achieves higher sensitivity and specificity, and preferred positive predictive value and negative predictive value. Meanwhile, the present disclosure allows for better predicting the genotype of B-ALL/LBL with KMT2A. In addition, the technical solutions of the present disclosure can be used for post-treatment MRD detection and can also be used for typing detection and MRD monitoring following CAR-T treatment.

BRIEF DESCRIPTION OF THE DRAWINGS

FIG. 1B shows the plots for a same specimen of B-ALL/LBL bone marrow.

Figure 1A:
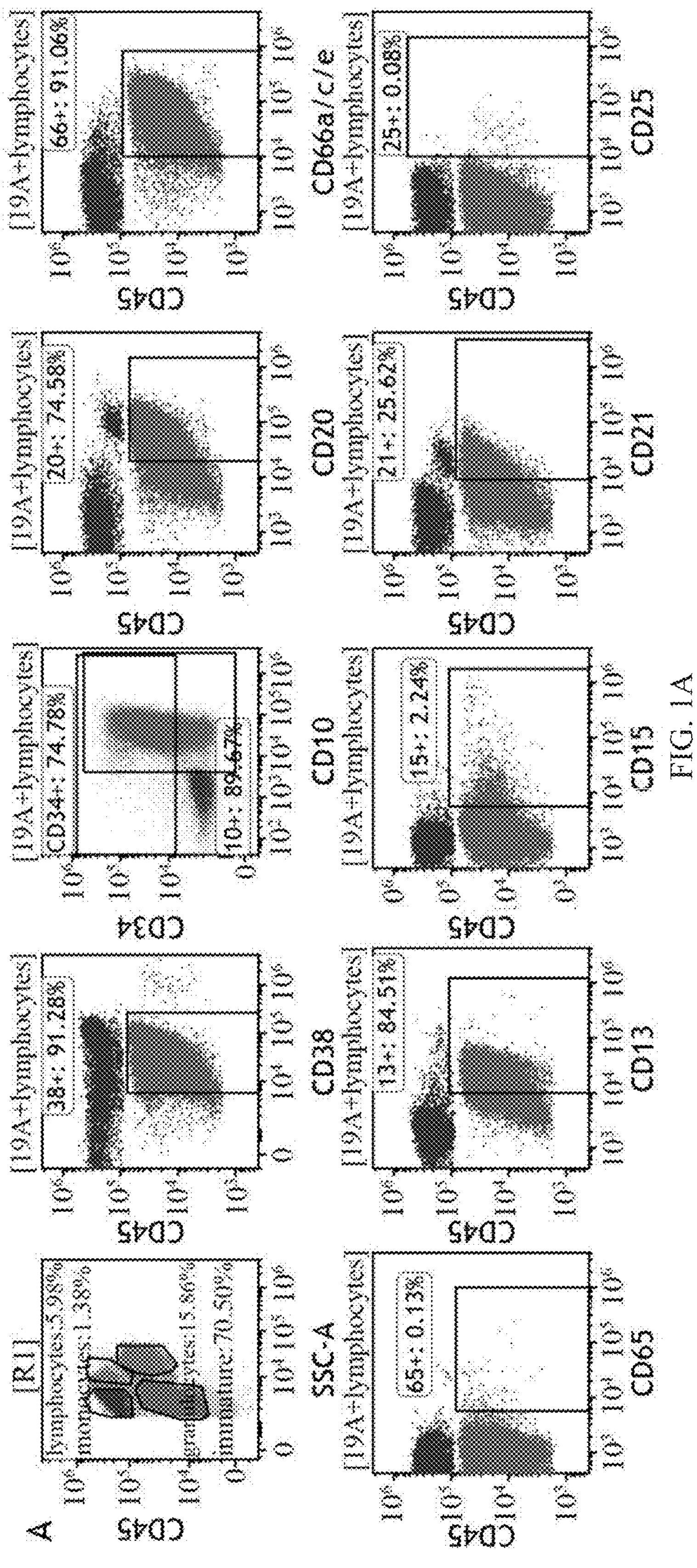
FIG. 1A and FIG. 1B show the methods for analyzing the expression of antigen-positive cells (%) in immature B cells by using the combination of the present disclosure (FIG. 1A) versus the conventional 10-color combination (FIG. 1B), and the comparison of antigen expression by using the two methods; where FIG. 1A

From FIG. 2A and FIG. 2B to FIG. 7A and FIG. 7B, each figure includes panel A and panel B. Panel B shows the test results of preliminary screening and panel A shows the test results obtained by using the antibody combination of the present disclosure.

DETAILED DESCRIPTION OF THE EMBODIMENTS

The following examples are used to illustrate the present disclosure but are not intended to limit the scope of the present disclosure. Unless otherwise specified, the technical means used in the embodiments are conventional means well known to those skilled in the art.

Unless otherwise specified, the experimental methods used in the following examples are conventional methods.

Unless otherwise specified, all materials and reagents in the following examples are commercially available sources.

In the present disclosure, flow cytometry is used to perform immunophenotype analysis on specimens such as bone marrow fluid, pleural effusion, and peripheral blood from clinical patients and to conduct further comprehensive immunophenotyping tests on the specimens that are identified as B-ALL/LBL following the primary screening. The 19-antibody combinations used in the primary screening are described in patent application No. 2021110670743.

Example 1 Preparation of Reagents

The present disclosure provides an antibody combination comprising a total of 20 antibodies, and the antibodies and compatible fluorescein were prepared according to the combinations in Table 3, wherein a combination of antibody and fluorescein is selected from antibody-fluorescein combination consisting of anti-CD22-SB436, anti-CD20-eFluor450, anti-CD21-BV480, anti-CD45-BV510, anti-CD10-BV605, anti-CD19-BV650, anti-CD24-BV711, anti-CD123-BV785, anti-CD65-FITC, anti-CD15-cFluorB548, anti-CD13-PE, anti-lambda-PE-Dazzle594, anti-HLA-DR-PE-Cy5, anti-CD34-PerCP-Cy5.5, anti-CD58-PerCP-Vio700, anti-CD81-PE-Cy7, anti-CD66a/c/e-AF647, anti-Kappa-eFluorR720, anti-CD38-APC-Fire750, and anti-CD25-APC-Fire810.

Preparation of Antibody combination: the above 20 antibodies were mixed in 1 container based on the dosage determined in a pre-experiment, and the resulting antibody combination was used for immunophenotyping and labeling of B-ALL/LBL specimens.

All of the above-mentioned antibodies can be directly purchased commercially, and the antibodies in the examples of the present disclosure are purchased from BD, Biolegend, Cytek, Invitrogen, or Beckman.

The above antibody combination was used to prepare a detection kit for detecting the immunophenotype of B-ALL/LBL. The kit also includes erythrocyte lysate and PBS, and the erythrocyte lysate can be prepared on-site or purchased commercially (for example, BD Company).

Example 2 Analysis of Immunophenotype of B-ALL/LBL Through Flow Cytometry Using 20-Color Antibody Combination The main materials and instruments of the experiment Materials: 10×PBS buffer solution, hemolysin dedicated for flow cytometer (BD company);

Instrument: CytekNL-3000 model full-spectrum flow cytometer, equipped with lasers having three wavelengths of 405 nm, 488 nm, and 635 nm, and 38 fluorescence detectors, Desktop low-speed centrifuge, and vortex mixer.

METHODS

Sample Collection

One to three millimeters of the human bone marrow fluid was collected and immediately placed in a heparin anticoagulant tube and quickly inverted several times to prevent the specimen from coagulating. Various cells in pleural effusion, lavage fluid, and the like were sent to the laboratory as soon as possible after collection, and the specimens were stored in a refrigerator at 4° C. The flow cytometry (FCM) must be completed within 48 hours and operated according to the instruction manual.

Process of Sample Preparation

Cell counting: 10 μl of bone marrow was added to 150 μl of PBS, mixed well, and Mindray FCM (model: mindray) was used to count the number of cells per microliter. The cell concentration was adjusted to $10\times10^6$/100 μl based on the test results, and 100 μl and 200 μl of cells were to be added to test tubes during detection when immunophenotyping and MRD were performed.

Staining of Antigen

The antibody premix solution for membrane labeling (labeled with corresponding fluorescein in Table 3) and the bone marrow specimen were added to each tube, mixed well, and incubated at room temperature in the dark for 15 min;

Hemolysis: 2 ml of 1×FACS hemolysin was added, mixed well by vortexing at low speed, and allowed to stand at room temperature in the dark for 8-10 min. The resulting mixture was washed by centrifugation at 300 g for 5 min. The supernatant was discarded.

Washing: 1 ml of PBS washing solution containing 0.1% $NaN_3$ and 1%-2% BSA was added and washed by centrifugation at 300 g for 5 min. The supernatant was discarded. 200 μl of PBS suspension cells was added for subsequent on-board assay.

On-Board Assay

Determination of optimum voltage and compensation: the voltage was set according to the conventional operation method for the spectral flow cytometer, and a single-stained sample for setting the instrument was prepared by referring to the fluorescence color matching of the kit.

Instrument setup, calibration, and quality control: the CytekNL-3000 was turned on to preheat for more than 20 minutes and rinsed with deionized water. Internal quality control was assayed to ensure that each test value was within a control range. The AL-PANAL was retrieved to load the sample and the data was collected.

On-board assay: According to the instrument conditions that had been set, 50,000 to 100,000 cells per tube were harvested during immunophenotyping, and 1 million cells per tube were harvested during MRD monitoring. If on-board assay was not conducted on the machine in time, 0.5 ml of 1% paraformaldehyde was added, mixed well, and stored in a refrigerator at 4° C., and the assay should be completed within 24 hours.

Results Analysis: Kluzaa Software was Used to Analyze the Data

Classification of Patient Cases

Debris, adherent cells, and dead cells were excluded, and gate R1 was set on living single cells.

The gate R1 cells were displayed, and a CD45/SSC plot was created. Gates were created on lymphocytes, monocytes, granulocytes, nucleated red blood cells, and immature cells according to the distribution of cells, and different colors were assigned to the cells. The immature cells of B-ALL/LBL were immature B cells. When gates were not well created on the immature B cells in the CD45/SSC plot, gates were set on $CD19^+$ B cells using CD45/CD19 or SSC/CD19. The populations of cells were observed to check whether the proportion was normal or whether the proportion of immature cells was increased, etc. In the normal bone marrow, the normal proportion range of each population of cells: lymphocytes: 20-40%, monocytes: 2-8%, granulocytes: 40-60%, nucleated red blood cells: 2-15%, and immature cells: less than 5%.

Series of two-dimensional dot plots of 2 antibodies were created, mainly including SSC/CD19, CD22/CD20, CD24/CD21, CD123/CD58, CD10/CD38, CD66/CD25, CD13/CD15, CD81/HLA-DR, CD65/CD81, and lambda/kappa, etc. All of these plots show the cells of gate R1. The expression of these antigens in immune B cells was analyzed. Antigen expression profiles are shown in Table 3.

Analysis of proportion (%) of positive cells expressing the antigen in immature B cells: a series of two-dimensional dot plots of 2 antibodies were created, with CD45 being selected for most of the ordinates, and different antibodies were selected for the abscissa, as shown in FIG. 1A. FIG. 1 also shows the immature B cells and $CD45^{st}$ normal lymphocytes. Since most of the detected antigens were negative in normal lymphocytes, they were used as negative controls, such as CD10 and CD34 in the figure to determine the positive boundary and to analyze the proportion (%) of positive cells expressing the antigen in immune B cells. Only CD38 and CD21 were partially positive in lymphocytes, and at this time, the lymphocytes expressed negatively were used to determine the boundary. The method for analyzing the expression of the 10-color combination antigen was the same as that for the 20-color combination, and the negative normal lymphocytes were used to determine the positive boundary.

Analysis of clonality of B cells: the expression of lambda and kappa in $CD19^+$ cells was analyzed. Normal B cells express lambda and kappa on the membrane surface at the mature stage, but not at the naive stage. If the neoplastic B cells express intracellular lambda or kappa but do not express membrane lambda or kappa, then they can be determined as Pre-B-ALL. If the neoplastic B cells express both intracellular lambda or kappa and membrane lambda plus kappa, then they need to be differentiated from B cells lymphoma.

Combined with the results for the preliminary screening tubes, for example, $MPO^-$ and $cCD3^-$ and expression of CD19, CD79a and/or CD22, then it met the criteria of the B series. At the same time, they conformed to the immature B cells phenotype, for example, expressing CD34, nTDT, or CD10, which supported the diagnosis of B-ALL/LBL. If the immature B cells did not express clambda or ckappa and the CD10 was negative, then the immature B cells were defined as Pro-B-ALL subtype; and if CD10 was expressed, then the immature B cells were defined as Com-B-ALL (Table 4). If clambda or ckappa antibody was expressed, then it was necessary to determine whether it was Pre-B-ALL according to the expression of lambda or kappa on the membrane surface. According to the method in 4 above, the percentage (%) of cells positively expressing CD33 in the primary screening tube was analyzed.

Result Judgment

Subtype judgment: combined with the results of primary screening, the B-ALL/LBL subtypes were judged according to Table 4.

TABLE 4

Typing of B-ALL/LBL subtypes and phenotypic characteristics

| Subtype | cCD79a | CD19 | CD34 | TdT | CD10 | ck or cl | k or l |
|---|---|---|---|---|---|---|---|
| Pro-B-ALL | + | + | +/− | + | − | − | − |
| Com-B-ALL | + | + | + | + | + | − | − |
| Pre-B-ALL | + | + | −/+ | +/− | + | + | − |

Determine the LAIP Markers

The antigen that is abnormally expressed in leukemia cells is called leukemia-associated immunophenotype (LAIP). LAIP is one of the important characteristics that distinguish leukemia cells from normal hematopoietic cells, and it is also a marker for flow cytometry to detect minimal residual disease (MRD). The antibody combination of the present disclosure is used to screen for LAIP in B-ALL/LBL patients and used for MRD monitoring.

LAIP Mainly Includes

For the expression of cross-series antigens or cross-lineage antigens, attention should be paid to whether the myeloid and T lineage-related antigens such as CD33, CD13, CD66, CD65, or CD25 are expressed. 2) The intensity of antigen expression is abnormal in antigens such as CD10, CD34, CD19, CD38, CD123, CD58, or CD81. 3) Abnormal clonality, whether the expression of kappa or lambda is restricted.

Judgment of genotype: some phenotypes are highly correlated with specific gene abnormalities. The detection of these markers allows for predicting whether there are any genetic abnormalities. According to the criteria in Table 2, a preliminary judgment is made on possible genetic abnormalities.

Screening for markers associated with treatment targets, including screening for the genotype of B-ALL/LBL with $BCR/ABL1^+$, antigen targets such as CD19 or CD22, and potential therapeutic targets. the present disclosure has established a scoring system for predicting the genotype of B-ALL/LBL with $BCR/ABL1^+$, which allows for predicting such diseases well, reminding clinicians to improve the examination of patient's gene and chromosome, and providing the doctors with important clues for choosing proper and specific therapies, which dramatically improves the prognosis of the patients. In addition, because the combination of the present disclosure aims at very comprehensive antibodies to be detected, it can not only report the expression of CD19 and CD22, but also provides favorable conditions for the screening of therapeutic targets to be developed in the future. Whether these targets are expressed, or the expression is enhanced or decreased provides a basis for the use of these targeted drugs.

MRD monitoring: One-tube 20-antibody combinations in the present disclosure can also be used for MRD monitoring of patients after treatment. The difference from immunophenotyping detection is that there is bigger amount of labeled cells and obtained cells. When using the flow cytometer to analyze the surface antigen of immature B cells, the LAIP phenotype is mainly analyzed. First, it is compared with newly diagnosed LAIP to observe whether LAIP-positive cells appear, and then it is compared with normal cells to analyze whether LAIP changes in B cells and whether new LAIP appears. If LAIP is present, then it can be identified as abnormal and neoplastic B cells, namely, MRD+.

Results

The originally designed combination in the present disclosure comprises 21 antibodies. Compared with Table 3, NG2-PE is additional, and another difference is that the antibody-fluorescein pairs are CD15-BV421 and CD13-APC. Now the antibody-fluorescein pairs are CD15-cFluor B548 and CD13-PE instead. Because the CD15-BV421 signal was too strong after using the initial combination to detect several samples, the CD13-APC test results were quite different from the usual PE and PE-Cy7 markers and interfered greatly with the Alexa Fluor647 channel. Because the PE-Cy7 channel is for CD81, which is not easy to be changed due to, NG2 is mainly used to detect patients with t (v;11q23.3); KMT2A rearrangement and the incidence rate of this type of B-ALL/LBL is overall low. Considering There are other antibodies in this combination to help diagnose such tumors, NG2 was discarded, the PE channel was changed to CD13, and the fluorescein matching CD15 was changed to a weaker fluorescein cFluor B548, forming the combination shown in Table 3. Using this antibody combination, a total of 67 bone marrow samples were detected, all of which passed the primary screening test, of which 5 were normal bone marrow samples and 62 were B-ALL/LBL samples. The first 44 B-ALL/LBL samples were used as an experimental group to establish a scoring system for predicting the subtype of the BCR/ABL1 gene. Afterward, 18 B-ALL/LBL specimens were tested for verification of the scoring system, which was named the verification group. The age, gender distribution, immune subtype, and genetic examination results for 62 B-ALL/LBL patients are shown in Table 5. Among them, 22 patients with t (9;22) (q34;q11.2); BCR/ABL1 were all adults, and 6 patients with t (12;21) (p13.2;q22.1);ETV6-RUNX All were children <14 years old, and 2 patients with t (v;11q23.3); KMT2A were children.

TABLE 5

Data and results for 62 patients with B-ALL/LBL

| | Experimental group | Verification group |
|---|---|---|
| Number of patients | 44 | 18 |
| Male versus female | 29:15 | 9:9 |
| <14 years old | 13 | 7 |
| Com subtype | 36 | 17 |
| Pro subtype | 8 | 0 |
| Pre subtype | 0 | 1 |
| t (9; 22) (q34; q11.2); BCR/ABL1 | 14 | 8 |
| t(12; 21) (p13.2; q22.1); ETV6-RUNX | 5 | 1 |
| t (v; 11q23.3); KMT2A | 3 | 0 |

Figure 1B:
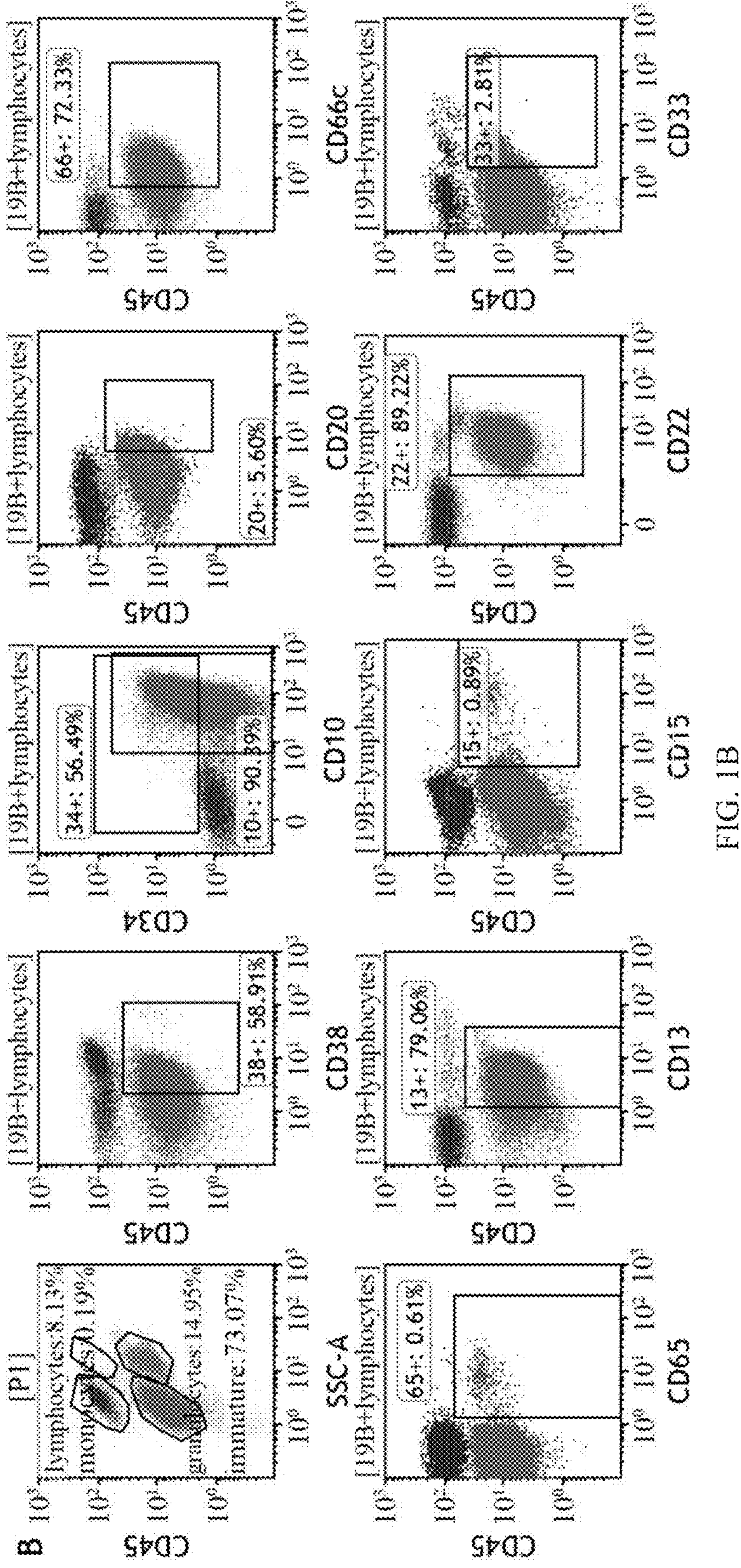

The expression of major antigens in the 20-color combination of 62 B-ALL/LBL specimens is shown in Table 6. Forty-two of the 44 B-ALL/LBL specimens in the experimental group underwent routine immunophenotyping tests at the same time, using a 10-color and 4-tube antibody combination. The composition of the 10-color antibody combination is shown in Table 7. There are 4 tubes in total, and the first tube is a screening tube. CD25, cCD22, and CD21 were not detected in the 10-color combination. The analysis method for antigen expression using the 10-color combination is the same as that for the 20-color combination, and normal lymphocytes with negative expression are used as the positive boundary. As shown in FIG. 1B, the results are shown in Table 6. Table 6 lists the detection results for the 20-color combination and the routine 10-color combination, and the numbers in the table represent the proportion of positive cells (%). Table 6 shows that only the proportion of CD38 is significantly higher than that of the conventional method, there is a significant difference between the experimental group and the verification group ($P<0.05$), and there is no significant statistical difference between the 20-color combination and 10-color combination for the antigen expression in the experimental group and the verification group. The difference for CD38 mainly lies in the stronger expression in the 20-color combinations. This does not affect the judgment of the results.

TABLE 6

Comparison of test results between 20-color and 10-color combonations (positive cells %)

| | Experimental group | | | | Verification group | | | |
|---|---|---|---|---|---|---|---|---|
| | 20 colors, N = 44 | | 10 colors, N = 42 | | 20 colors, N = 18 | | 10 colors, N = 17 | |
| | Mean | Standard deviation | Mean | Standard deviation | Mean | Standard deviation | Mean | Standard deviation |
| CD34 | 81.22 | 31.45 | 75.42 | 33.80 | 59.78 | 40.78 | 50.18 | 42.42 |
| CD10 | 76.11 | 38.45 | 87.77 | 28.15 | 89.80 | 23.36 | 99.18 | 2.29 |
| CD20 | 22.15 | 32.21 | 19.97 | 25.16 | 27.33 | 37.86 | 21.88 | 31.55 |
| CD22 | 53.83 | 30.08 | 64.93 | 29.39 | 48.03 | 28.00 | 48.07 | 32.29 |
| CD24 | 87.02 | 25.51 | 85.21 | 19.32 | 94.39 | 9.45 | 87.97 | 23.56 |
| CD66 | 37.19 | 33.19 | 26.08 | 28.75 | 33.29 | 33.54 | 14.32 | 18.32 |
| CD38* | 83.79 | 23.77 | 67.02 | 26.44 | 86.97 | 17.32 | 56.83 | 36.70 |
| CD15 | 6.35 | 9.70 | 4.34 | 9.95 | 9.84 | 11.40 | 3.91 | 4.06 |
| CD65 | 1.82 | 5.90 | 1.34 | 1.82 | 0.84 | 1.59 | 0.65 | 0.60 |
| CD123 | 75.27 | 21.61 | 81.32 | 19.02 | 65.37 | 30.42 | 65.35 | 30.83 |
| CD58 | 81.61 | 21.90 | 69.94 | 27.22 | 63.15 | 34.41 | 69.29 | 33.67 |
| CD81 | 65.84 | 32.48 | 68.25 | 29.12 | 61.34 | 36.22 | 72.11 | 36.76 |
| HLA-DR | 84.00 | 20.77 | 90.92 | 12.86 | 91.28 | 12.37 | 91.48 | 10.29 |
| CD13 | 15.74 | 26.23 | 16.98 | 26.34 | 22.54 | 30.24 | 25.63 | 32.86 |
| CD21 | 15.69 | 27.55 | | | 25.78 | 33.21 | | |
| CD25 | 9.18 | 20.32 | | | 51.98 | 34.41 | | |

Note:
N: number of cases;
*experimental group and verification group $P < 0.05$

TABLE 7

Composition of conventional 10-color antibody combination

| Tube | FITC | PE | PerCP-cy5.5 | PE-CY7 | APC | APC-R700 | APC-CY7 | BV421 | V500 | BV605 |
|---|---|---|---|---|---|---|---|---|---|---|
| 1 | CD34 | CD10 | CD7 | CD19 | CD38 | CD38 | CD56 | CD117 | CD45 | CD5 |
| 2 | CD65 | CD66c | CD22 | CD123 | CD43 | | HLA-DR | CD8 | CD45 | CD19 |
| 3 | CD58 | NG2 | CD34 | CD13 | CD38 | | CD24 | CD15 | CD45 | CD19 |
| 4 | TdT | clambda | CD79a | ckappa | | | CD20 | cIgM | CD45 | CD19 |

By analyzing the proportions of antigen-positive cells in 14 patients with BCR/ABL1$^+$ and in 30 patients with BCR/ABL1$^-$ B-ALL/LBL in the experimental group (Table 8), it can be seen that the expression of CD20, CD21, CD25, CD66, CD38, and CD13 varies between groups. By identifying the patients having a proportion of positive cells >20% as positive patients, we calculated the proportions of positive patients in the two groups of patients, as shown in Table 9. The results in Table 9 show that using any antigen as a marker to distinguish between two groups of B-ALL/LBL does not allow for meeting the requirements for both high sensitivity and high specificity. However, CD20, CD21, CD38$^{dim}$, CD66, CD25, and CD13 were scored as 6 markers, each positive antigen was scored as 1 point. For the score ≥3 points, it was predicted as BCR/ABL1$^+$, and <3 points as BCR/ABL1$^-$. In the BCR/ABL1$^+$ and the BCR/ABL1$^+$ patients, the sensitivity and specificity were 92.86% and 90.0% (Table 9), respectively, and the positive predictive value and negative predictive value were 81.25% and 96.42%, respectively. It can better predict the subtype of BCR/ABL1 gene.

| N = 44 | Gene positive | Gene negative |
|---|---|---|
| CD34 | 79.76 | 84.53 |
| CD10 | 73.72 | 81.58 |
| CD20 | 14.57 | 39.47 |
| CD21 | 7.53 | 34.35 |
| CD22 | 51.21 | 59.82 |
| CD24 | 84.65 | 92.45 |
| CD25 | 3.82 | 21.42 |
| CD66 | 32.48 | 47.95 |
| CD38 | 77.43 | 66.29 |
| CD15 | 6.48 | 6.03 |
| CD65 | 2.32 | 0.68 |
| CD123 | 66.87 | 62.99 |
| CD58 | 80.11 | 85.05 |
| CD81 | 71.88 | 52.06 |
| HLA-DR | 84.38 | 83.12 |
| CD13 | 11.39 | 25.69 |

TABLE 9

Scoring results for BCR/ABL1$^{+/-}$ B-ALL/LBL using the 20-color combination in the experimental group

| Gene grouping | Antigen positive | CD20 | CD21 | CD38$^{dim}$ | CD66 | CD25 | CD13 | Score ≥3 |
|---|---|---|---|---|---|---|---|---|
| Negative | n | 8 | 6 | 13 | 15 | 1 | 7 | 3 |
| N = 30 | % | 26.67 | 20.00 | 43.33 | 50.00 | 3.33 | 23.33 | 10.00 |
| Positive | n | 8 | 8 | 11 | 11 | 4 | 6 | 13 |
| N = 14 | % | 57.14 | 57.14 | 78.57 | 78.57 | 28.57 | 42.86 | 92.86 |

Note:

N indicates the total number of patients, n indicates the number of patients with positive antigen expression

TABLE 10

Experimental group 10 color combination to BCR/ABL1$^{+/-}$ B-ALL/LBL integration results

| Gene grouping | Antigen positive | CD20 | CD38$^{dim}$ | CD66 | CD13 | CD33 | Score ≥3 |
|---|---|---|---|---|---|---|---|
| Negative | n | 7 | 16 | 12 | 6 | 13 | 7 |
| N = 28 | % | 25.00 | 57.14 | 42.86 | 21.43 | 46.43 | 25.00 |
| Positive | n | 5 | 11 | 7 | 6 | 6 | 7 |
| N = 14 | % | 35.71 | 78.57 | 50.00 | 42.86 | 42.86 | 50.00 |

Note:

N indicates the total number of patients, n indicates the number of patients with positive antigen expression For the patients detected by using a conventional 10-color antibody combination, since CD21 and CD25 were not detected simultaneously, 5 markers, CD20, CD38$^{dim}$, CD66, CD13, and CD33 (results of primary screening tubes) were used for scoring, with each positive antigen being scored as 1 point. A score of ≥3 points was predicted as BCR/ABL1$^+$, and score of <3 points was predicted as BCR/ABL1$^-$. For the prediction of the subtype of B-ALL/LBL with t (9;22) (q34;q11.2); BCR/ABL1, the sensitivity and specificity were 50% and 75%, respectively (Table 10), and the positive predictive value and negative predictive value were 50% and 75%, respectively. If CD33 is removed, the remaining 4 parameters are scored, a score of ≥2 points is predicted to be BCR/ABL1$^+$, and <2 points are predicted to be BCR/ABL1$^-$. The predicted sensitivity and specificity were 78.57% and 46.43%, respectively, and the positive predictive value and negative predictive value were 45.83% and 72.22%, respectively. It is shown that the two scoring methods for the 10-color combination have poor practicability.

After the analysis of 44 patient cases in the experimental group, another 18 B-ALL/LBL specimens were detected subsequently, and these specimens were verified using the scoring system established above. Among them, 8 patients were BCR/ABL1 gene positive, and 10 patients were gene negative (including 1 patient with t (12;21) (p13.2;q22.1); ETV6-RUNX1). The results are shown in Table 11.

In the verification group, 17 patients underwent conventional 10-color combination detection at the same time, and 1 patient was gene negative specimens underwent only 20-color detection. The results are shown in Table 12. It can be seen from Table 11-12 that either a 20-color combination or a conventional 10-color combination provides similar sensitivity and specificity to that in the experimental group. At the same time, it is shown that the 20-color combination of the present disclosure is significantly better than the conventional 10-color detection, and the 6-point scoring system can well predict the subtype of BCR/ABL1 gene.

TABLE 11

Scoring results for BCR/ABL1$^{+/-}$ B-ALL/LBL in the verification group by using a 20-color combination

| Gene grouping | Antigen positive | CD20 | CD21 | CD38$^{dim}$ | CD66 | CD25 | CD13 | Score ≥3 |
|---|---|---|---|---|---|---|---|---|
| Negative | N | 2 | 1 | 2 | 2 | 0 | 3 | 0 |
| N = 10 | % | 22.22 | 11.11 | 22.22 | 22.22 | 0.00 | 33.33 | 0.00 |
| Positive | N | 4 | 7 | 6 | 5 | 4 | 2 | 7 |
| N = 8 | % | 50.00 | 87.50 | 75.00 | 62.50 | 50.00 | 25.00 | 87.50 |

Note:
N indicates the total number of patients, n indicates the number of patients with positive antigen expression

TABLE 12

Scoring results for BCR/ABL1$^{+/-}$ B-ALL/LBL in the verification group by using the 10-color combination

| Gene grouping | Antigen positive | CD20 | CD38$^{dim}$ | CD66 | CD13 | CD33 | Score ≥3 |
|---|---|---|---|---|---|---|---|
| Negative | n | 2 | 3 | 2 | 2 | 3 | 0 |
| N = 9 | % | 22.22 | 33.33 | 22.22 | 22.22 | 33.33 | 0.00 |
| Positive | n | 2 | 5 | 3 | 2 | 5 | 5 |
| N = 8 | % | 25.00 | 62.50 | 37.50 | 25.00 | 62.50 | 62.50 |

Note:
N indicates the total number of patients, n indicates the number of patients with positive antigen expression All of the Five patients with B-ALL/LBL with t (12;21) (p13.2;q22.1);ETV6-RUNX1 were children, and the phenotype was consistent with that reported in the above literature, all of them were of Com-B-ALL subtype and did not express CD66 and CD20. At the same time, CD22 was weakly expressed, and CD25, CD13, CD65, and CD15 were not expressed. Only 1 patient expressed CD38$^{dim}$.

Three patients with B-ALL/LBL with t (v;11q23.3); KMT2A rearrangement, 2 patients were 8 years old, and 1 patient was 71 years old, all of them were of Pro-B-ALL subtypes, which was consistent with literature reports. And all three patients expressed CD65 and CD15, expressed CD38 strongly, and did not express CD24. The immunophenotype of one child patient strongly suggested being B-ALL/LBL with t (v;11q23.3);KMT2A rearrangement, the chromosome was t (3:11) (q23,q23) after investigation, and a small number of children expressed CD117, which was consistent with that reported in a large number of children. All patients with B-ALL/LBL of the remaining subtypes did not express CD65, CD15, and CD117, indicating that the specificity of these three antibodies was very high, which was of great help in predicting such genotyping. Therefore, for Pro-B-ALL subtype patients, if the expression of CD65, CD15, and CD117, then it suggests B-ALL/LBL with t (v;11q23.3);KMT2A rearrangement.

Because there were rare patients with B-ALL/LBL with t (12;21) (p13.2;q22.1); ETV6-RUNX1 and B-ALL/LBL with t (v;11q23.3); KMT2A rearrangement, scoring and predictive analysis were not performed.

At present, major progress in the treatment of B-ALL/LBL is the application of antigen-specific targeted therapy. The most commonly used therapies for antigens CD19 and CD22 are CD19-CAR-T or CD22-CAR-T, as well as dual CAR-T therapy of CD19-CAR-T combined with CD22-CAR-T. After the CAR-T therapy, these patients may experience CD19 and CD22 negative relapses. For these patients, gating strategies other than CD19 or CD22 need to be used to gate the immature B cells. The analysis results of antigen expression in patients in the present disclosure showed that CD24 was strongly positive except for the specimens with t (v;11q23.3);KMT2A, and the mean+standard deviation of percentage of cells positively expressing CD24 was 92.63%+14.21%. Therefore, in the specimens obtained from the patients after receiving CD19-CAR-T or CD22-CAR-T treatment, B-ALL/LBL can be divided into two types, the first category is B-ALL/LBL with t (v;11q23.3); KMT2A genotype, and the second type is other B-ALL/LBL types. For the second type, CD24 can be used to gate the B cells. Because CD24 was also expressed on the surface of granulocytes, monocytes, and T cells, and CD15 was almost only expressed in the genotype oft (v;11q23.3); KMT2A. Therefore, firstly, a first gate J was created on CD24$^{+}$CD15$^{-}$ cells (FIG. 8) in the CD24/CD15 plot to exclude granulocytes and monocytes. Secondly, a CD45/SSC plot was created and a gate was set on B cell for SSC low CD45− cells, which excluded CD45$^{+}$ T cells. The expression of CD34, CD10, CD123, CD81, etc. in the B cell gate was further confirmed to be the immature B cells, and the B cell gate can be further defined to make the proportion of immature B cells more accurate.

For the patients with the first type of genotype of B-ALL/LBL with t (v;11q23.3);KMT2A, because they do not express CD24, or even CD10, CD22 or CD20, but express CD34 and strongly express CD38, the immature B cells can be gated using CD45/CD38 and CD13/SSC (FIG. 9) after being treated with CD19-CAR-T. First, a gate J for CD45$^{dim+}$CD38$^{+}$ cells was set in the CD45/CD38 plot to exclude mature red blood cells and lymphocytes, and then a gate B cell for SSC low CD13$^{-}$ cells in the CD13/SSC plot was set to exclude granulocytes, immature myeloid cells, and monocytes. Inside the door were the immature B cells. Since patients of this genotype express CD34$^{+}$, CD65, and CD15. These markers can be used to further help to judge abnormal immune B cells as MRD markers. Therefore, the two gating methods for CD24 and CD38 can be used for typing detection and MRD monitoring of all B-ALL/LBL patients after receiving CD19-CAR-T and CD22-CAR-T therapies. The advantage is that it eliminates the need to detect intracellular antigens, reduces operation steps, saves time, and avoids false negatives caused by incorrect labeling of intracellular antigens.

Since the combination of the present disclosure contains more antibodies, it provides a notable advantage for the recognition of B cells. For other potential therapeutic targets in the combination, such as CD123, CD58, CD20, CD81, etc., the above gating method can still be used for testing. If CD24$^{-}$CAR-T appears in the future, CD10/SSC or CD34/SSC can still be used to gate CD10$^{+}$ or CD34$^{+}$ SSC low cells, and then combined with other antigens of the combination of the present disclosure to confirm the B cells. At present, CD38-CAR-T is mainly used for the treatment of plasma cell diseases, and there has been no report on ALL-B.

FIG. 1 FIG. 1A and FIG. 1B show a specimen of B-ALL/LBL bone marrow, showing the method for analyzing the proportion (%) of positive cells expressing antigen in immature B cells. At the same time, the present disclosure combination (A) and the conventional 10-color combination of our laboratory (B) were compared for the test results. FIG. 1A and FIG. 1B show two populations of cells including immune B cells and CD45$^{st}$ normal lymphocytes. Normal lymphocytes were used as control cells to determine the positive boundary, which was used to analyze the proportion (%) of positive cells expressing the antigen in immune B cells. Most of the antigens shown in the figure are negative in lymphocytes, and only CD38 and CD21 are partially positive in lymphocytes. At this time, lymphocytes with negative expression are used as the positive boundary. FIG. B shows that in the 10-color combination, the analysis method is the same as that for the 20-color combination, and the normal lymphocytes with negative expression are used as the positive boundary. FIG. 1B shows that CD38, CD20, CD66, and CD13 are all positive in the 10-color combination, but the proportions are all lower than those in the 20-color combination (FIG. 1A). The results are consistent with the diagnosis of B-ALL/LBL while affecting the judgment of genotype.

Figure 2A:
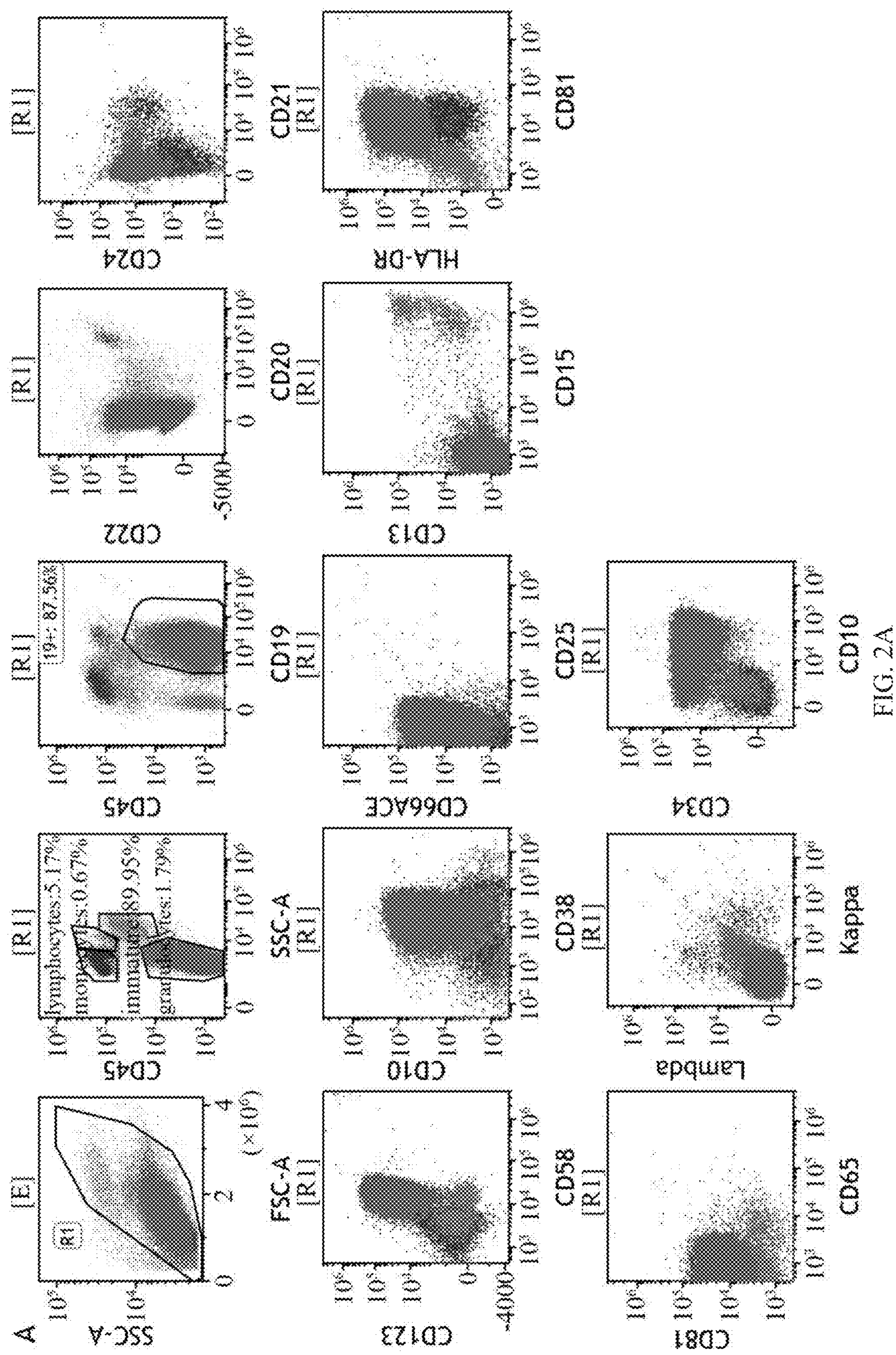
FIG. 2A and FIG. 2B show the test result of a patient with B-ALL-COM.
Figure 2B:
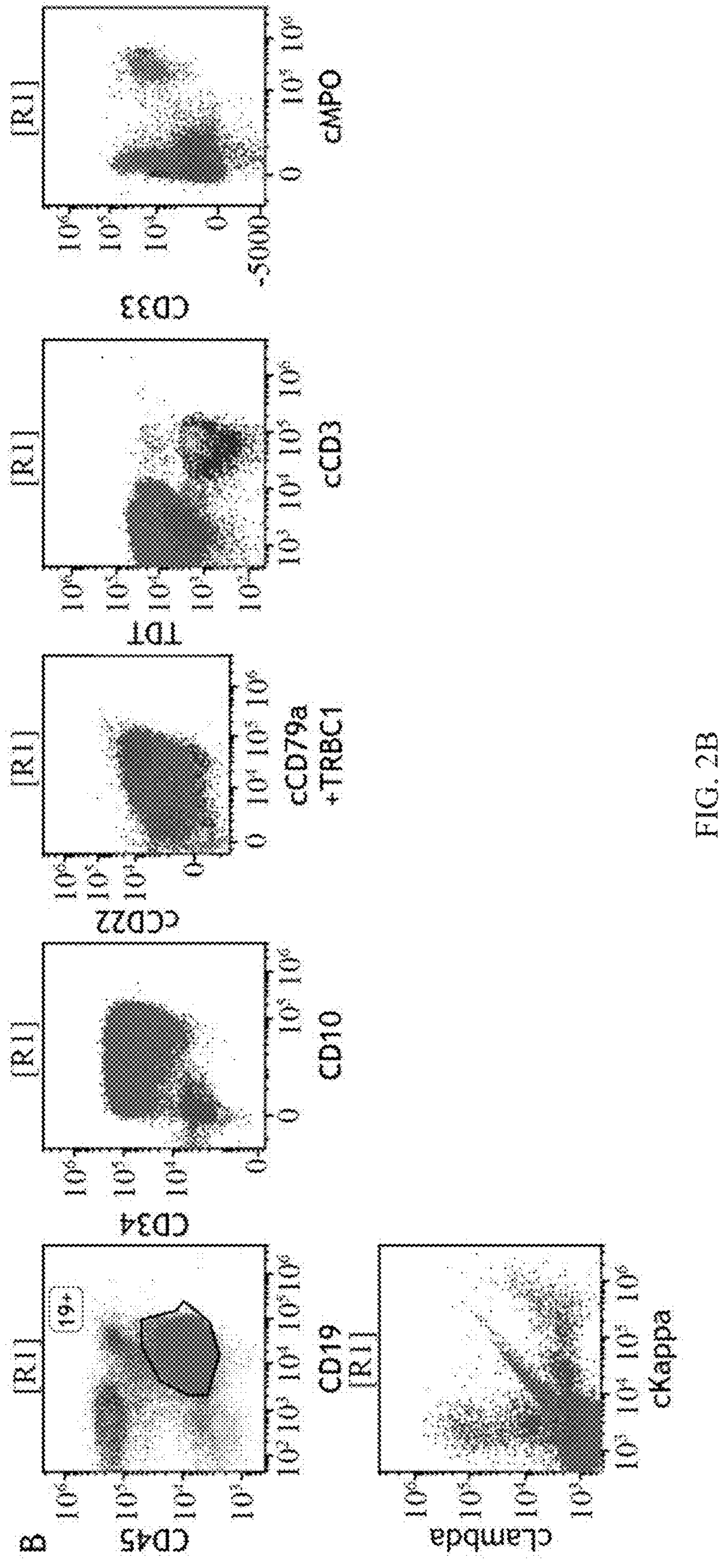

FIG. 2A and FIG. 2B show the test results of B-ALL-Com. FIG. 2A shows the test results for the antibody combination of the present disclosure and FIG. 2B shows the result for the early screening tube. FIG. 2B proves that the immature cells express CD19, CD10, CD34, nTdT, cCD79a, and cCD22, but do not express ckappa or clambda, and the immature cells are of B-ALL-Com subtype. The immature cells do not express cMPO or cCD3, except AML and T-ALL. Furthermore, the antibody combination of the present disclosure was used to judge B-ALL/LBL genotype and LAIP. In FIG. 2A, the CD45/CD19 plot shows that CD19$^{+}$ B cells account for 87.56%, express CD22, CD24, CD123, CD58, CD66, HLA-DR, and CD81, and do not express CD20, CD21, CD13, CD15, CD25, CD65, Kappa, or lambdas. Since it does not express CD20, CD21, CD13, and CD25, and CD38 is not weakly expressed, it expresses only CD66, with a score of 1, and does not support B-ALL/LBL with BCR/ABL1. According to the expression of CD66, does not support B-ALL/LBL with ETV6-RUNX1. Based on CD10 positivity and CD15 and CD65 negativity, B-ALL/LBL with t (v;11q23.3) is not supported. LAIP:CD19$^{+}$CD34$^{+}$CD45$^{-}$CD123$^{+}$CD66$^{+}$. There was no recurrent genetic abnormality in this patient through genetic and chromosome examination and the results of immunophenotyping were supported.

Figure 3A:
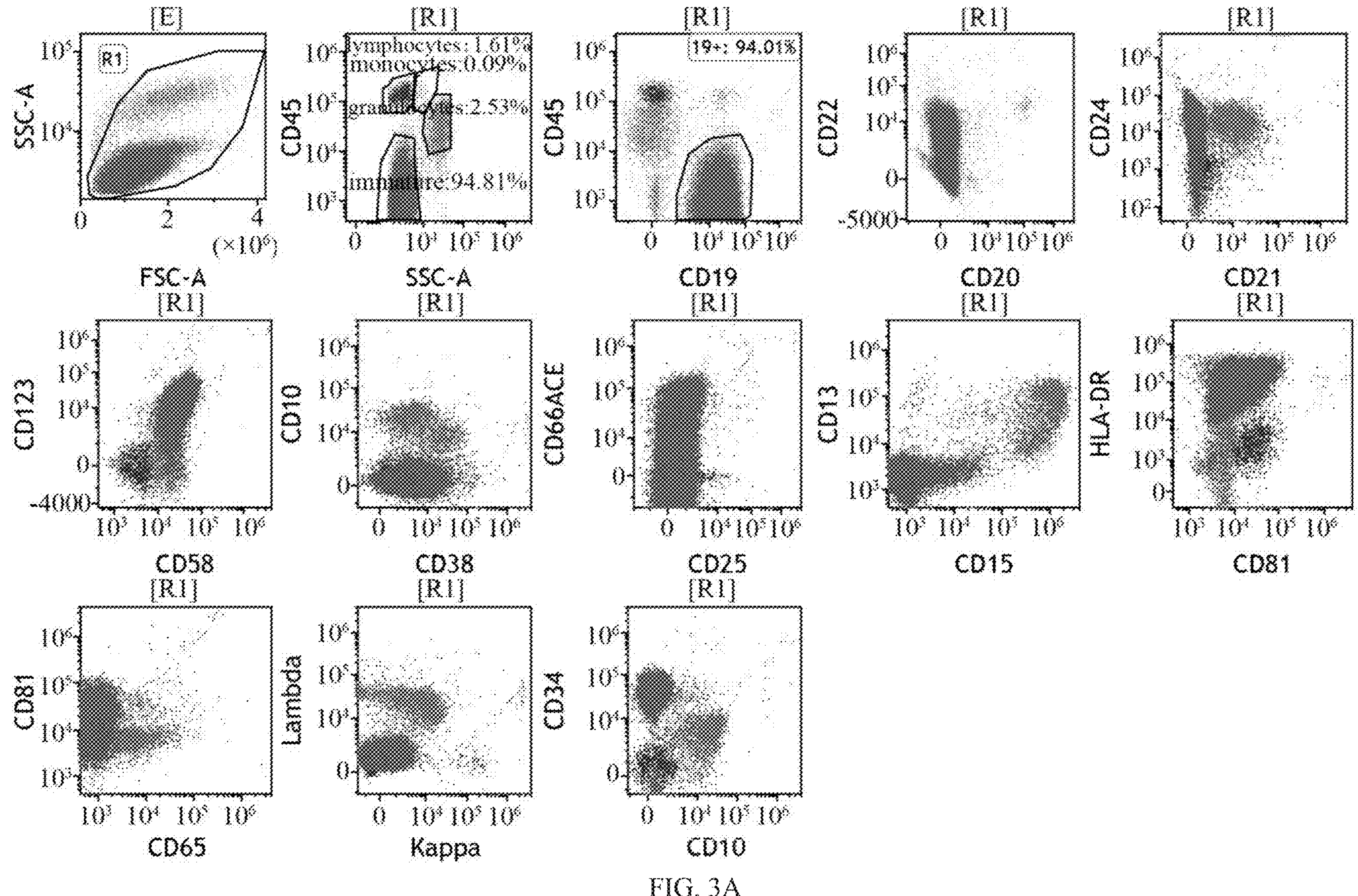
FIG. 3A and FIG. 3B show the test result for a case of B-ALL-PRO.
Figure 3B:
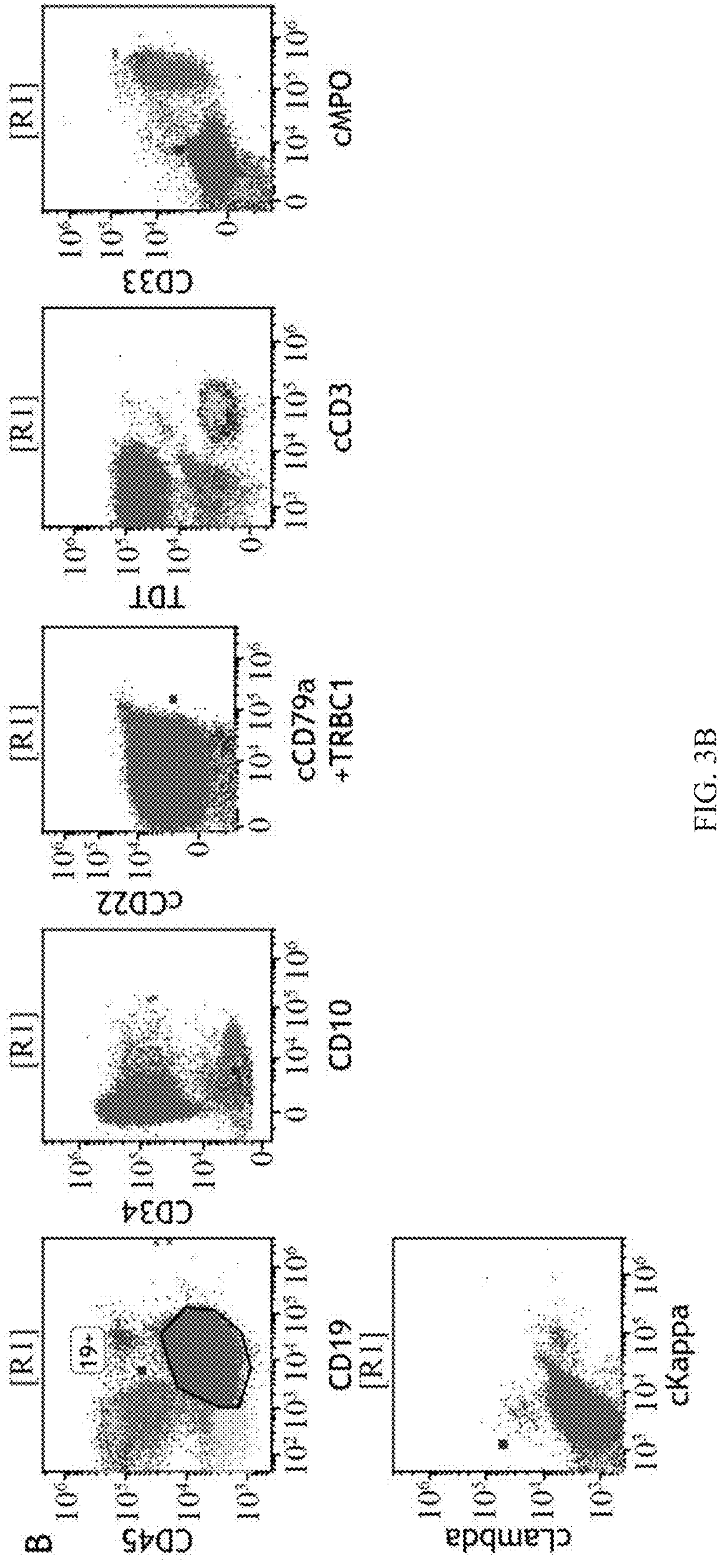

FIG. 3A and FIG. 3B show the test results of a patient with B-ALL-Pro. FIG. 3A shows the test results for the antibody combination of the present disclosure and FIG. 3B shows the result for the early screening tube. FIG. 3B proves that the immature cells express CD19, CD34, nTdT, cCD79a, and cCD22, but do not express CD10, ckappa or clambda. They are of B-ALL-Pro subtype and do not express cMPO or cCD3, except for AML and T-ALL. Furthermore, the antibody combination of the present disclosure was used to judge B-ALL/LBL genotype and LAIP. In the CD45/SSC and CD45/CD19 plots of FIG. 3A, it is shown that the immature cells and CD19$^{+}$ B cells account for 94%, and they express CD22, CD24, CD123, CD58, HLA-DR, and CD81$^{dim}$, partially express CD38 and CD66, and do not express CD10, CD20, CD21, CD13, CD15, CD25, CD65, kappa or lambda. Due to partial expression of CD38 and CD66 but no expression of CD20, CD21, CD13 or CD25, it scores 2 points. B-ALL/LBL with BCR/ABL1 is not supported; B-ALL/LBL with ETV6-RUNX1 is not supported based on CD66 expression; and B-ALL/LBL with t (v;11q23.3) is not supported based on CD15 and CD65 negativity. LAIP:CD19$^{+}$CD10$^{-}$CD34$^{+}$CD123$^{+}$CD58$^{+}$CD38$^{dim+}$. There was no recurrent genetic abnormality in this patient through genetic and chromosome examination and the results of immunophenotyping were supported.

Figure 4A:
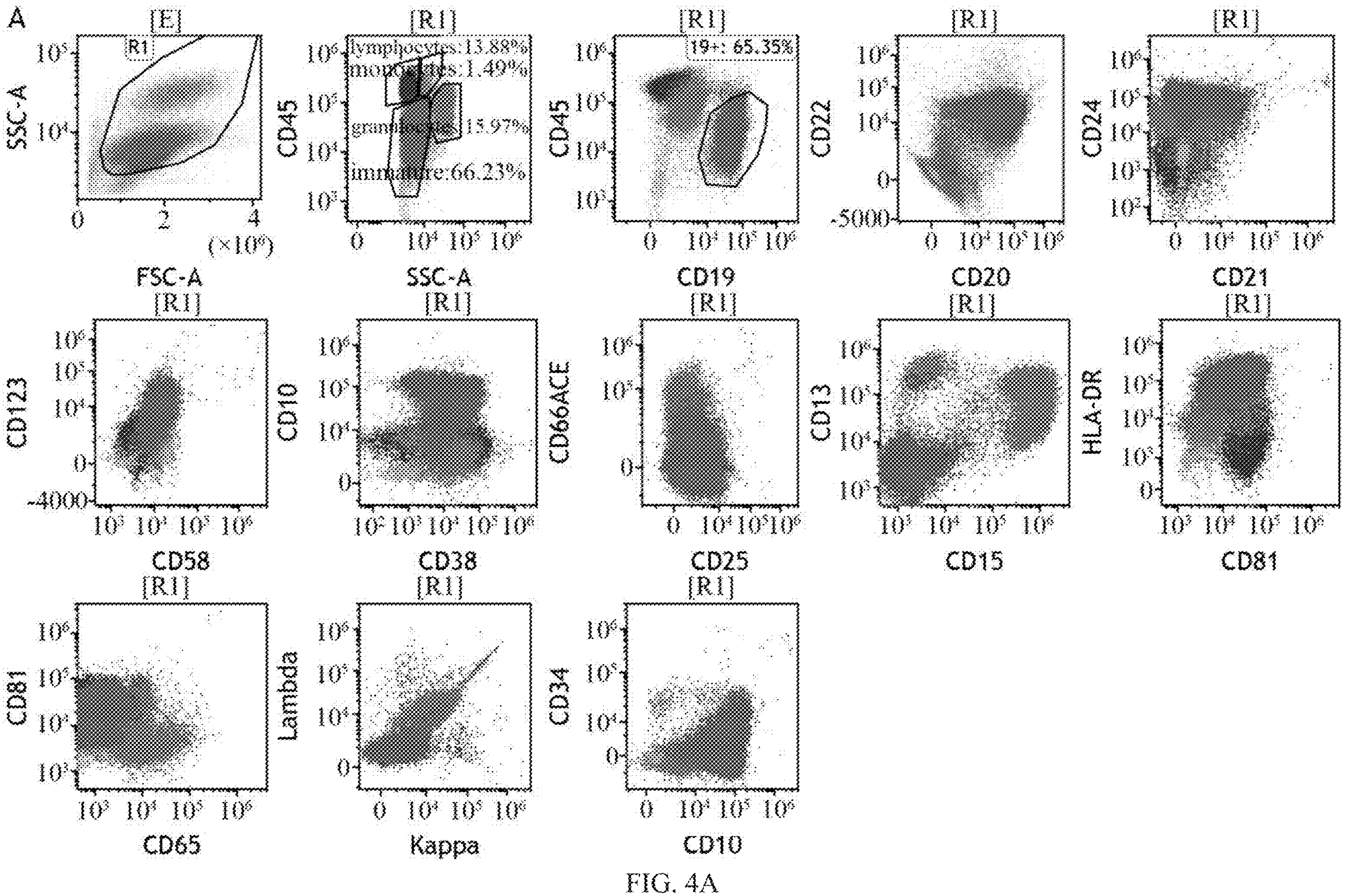
FIG. 4A and FIG. 4B show the test result of a patient with B-ALL/LBL with t (9;22) (q34;q11.2); BCR/ABL1.
Figure 4B:
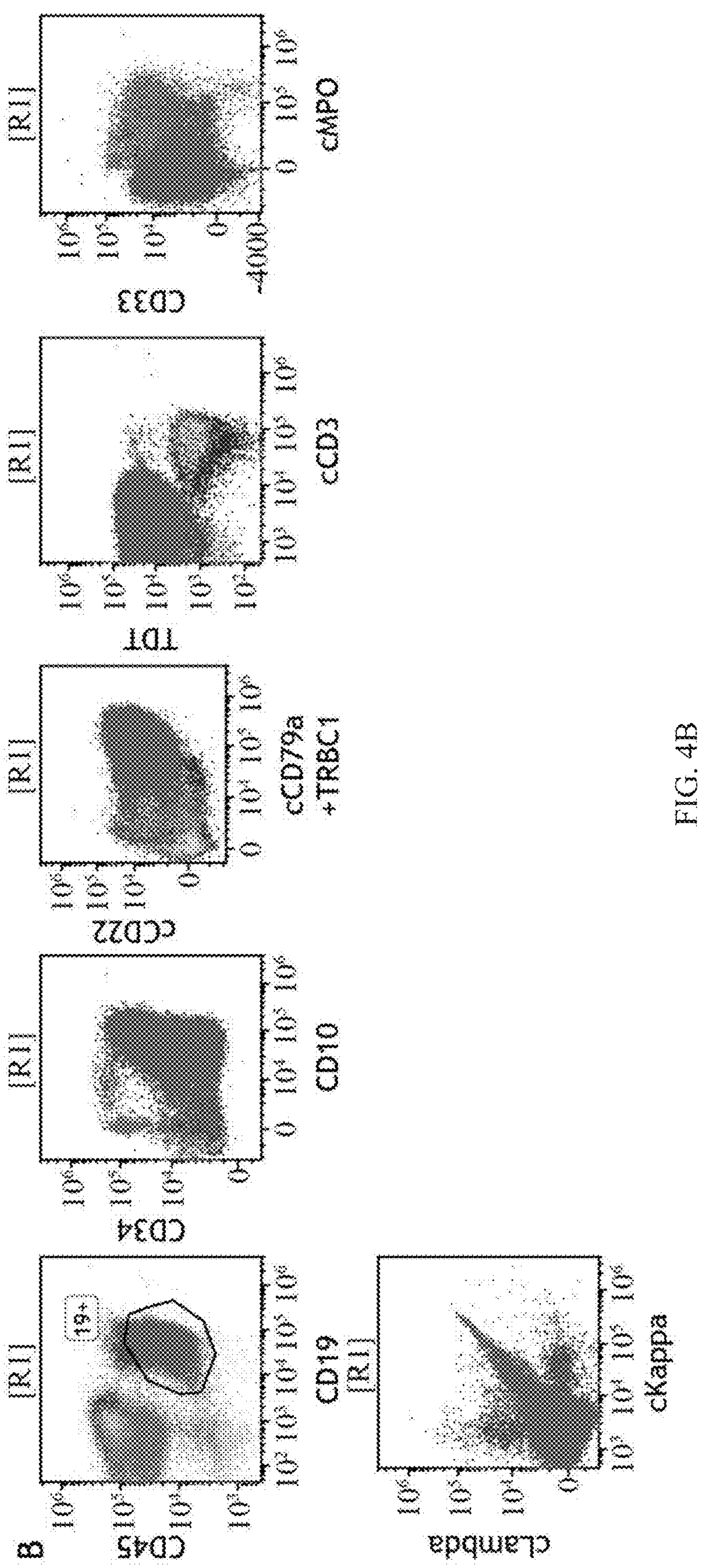

FIG. 4A and FIG. 4B show the test results in a patient with B-ALL/LBL with t (9;22) (q34;q11.2); BCR/ABL1. FIG. 4A shows the test results for the antibody combination of the present disclosure, and FIG. 4B shows the result for the early screening tube. FIG. 4B proves that the immature cells express CD19, CD10, nTdT, cCD79a, and cCD22, partially express CD34 or CD33 and do not express ckappa or clambda, thus they are of the B-ALL-Com subtype and do not express cMPO or cCD3, except for AML and T-ALL. Furthermore, the antibody combination of the present disclosure was used to judge B-ALL/LBL genotype and LAIP. In the CD45/SSC plot and CD45/CD19 plot of FIG. 4A, it is shown that the immature cells and CD19+ B cells account for 65-66%, and they express CD22, CD20, CD24, CD123, CD58, HLA-DR, CD38$^{dim}$, and CD81$^{dim}$, partially express CD21, CD66, and does not express CD13, CD25, CD15, CD65, kappa, or lambda. Based on the expression of CD20, CD38$^{dim}$, CD21, and CD66, they scored 4 points, which supports B-ALL/LBL with BCR/ABL1. Based on the expression of CD20, it does not support B-ALL/LBL with ETV6-RUNX1. Based on the negative CD15 and CD65, it appears that it is not B-ALL/LBL with t (v;11q23.3). LAIP: CD19$^{+}$CD10$^{+}$CD34$^{+}$CD123$^{+}$CD58$^{+}$CD38$^{dim+}$. Through gene test, the test result of the patient was BCR/ABL1 fusion gene positive, which proved to be B-ALL/LBL with BCR/ABL1.

Figure 5A:
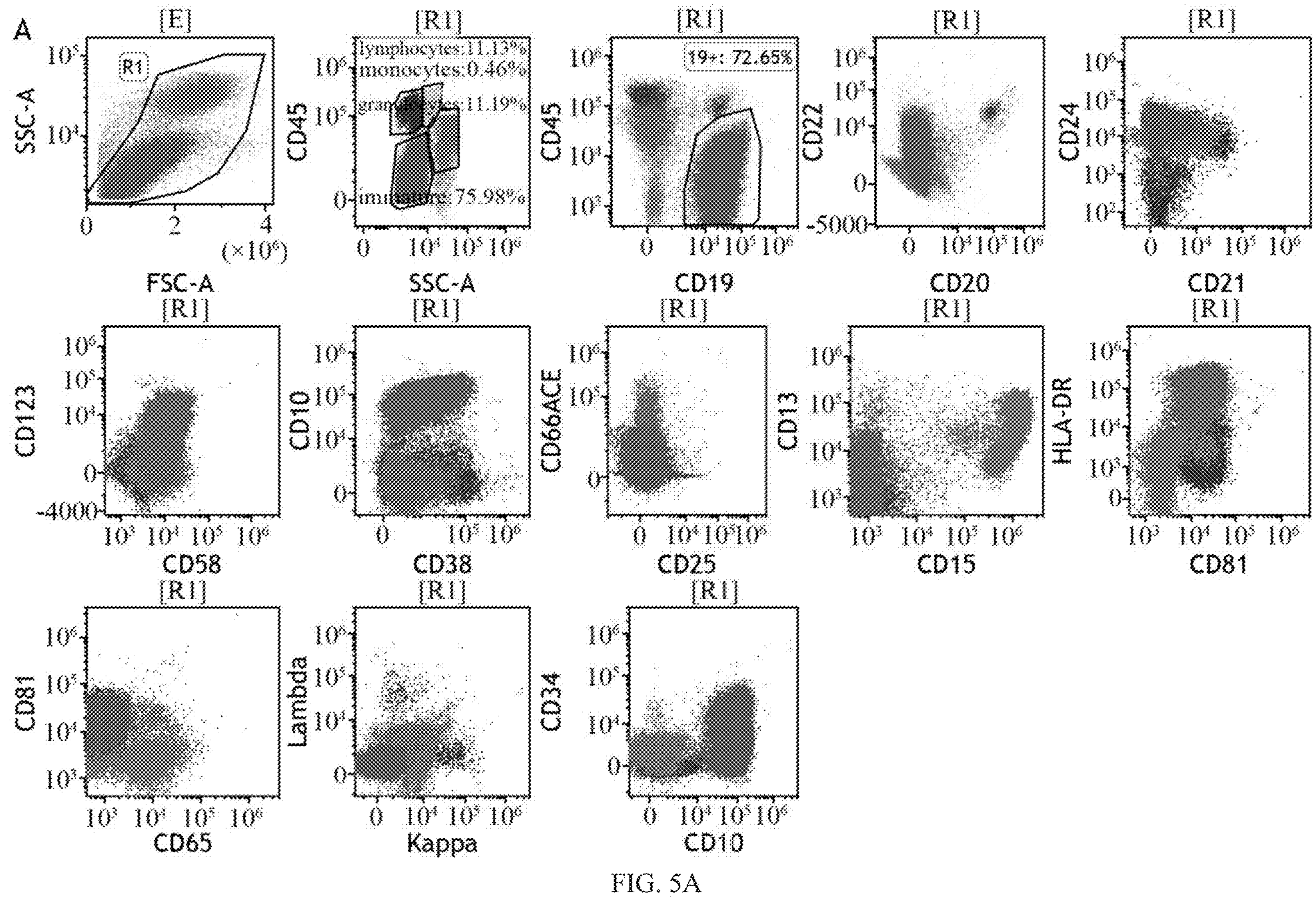
FIG. 5A and FIG. 5B show the test result of a patient with B-ALL/LBL with t (12;21) (p13.2;q22.1); ETV6-RUNX1.
Figure 5B:
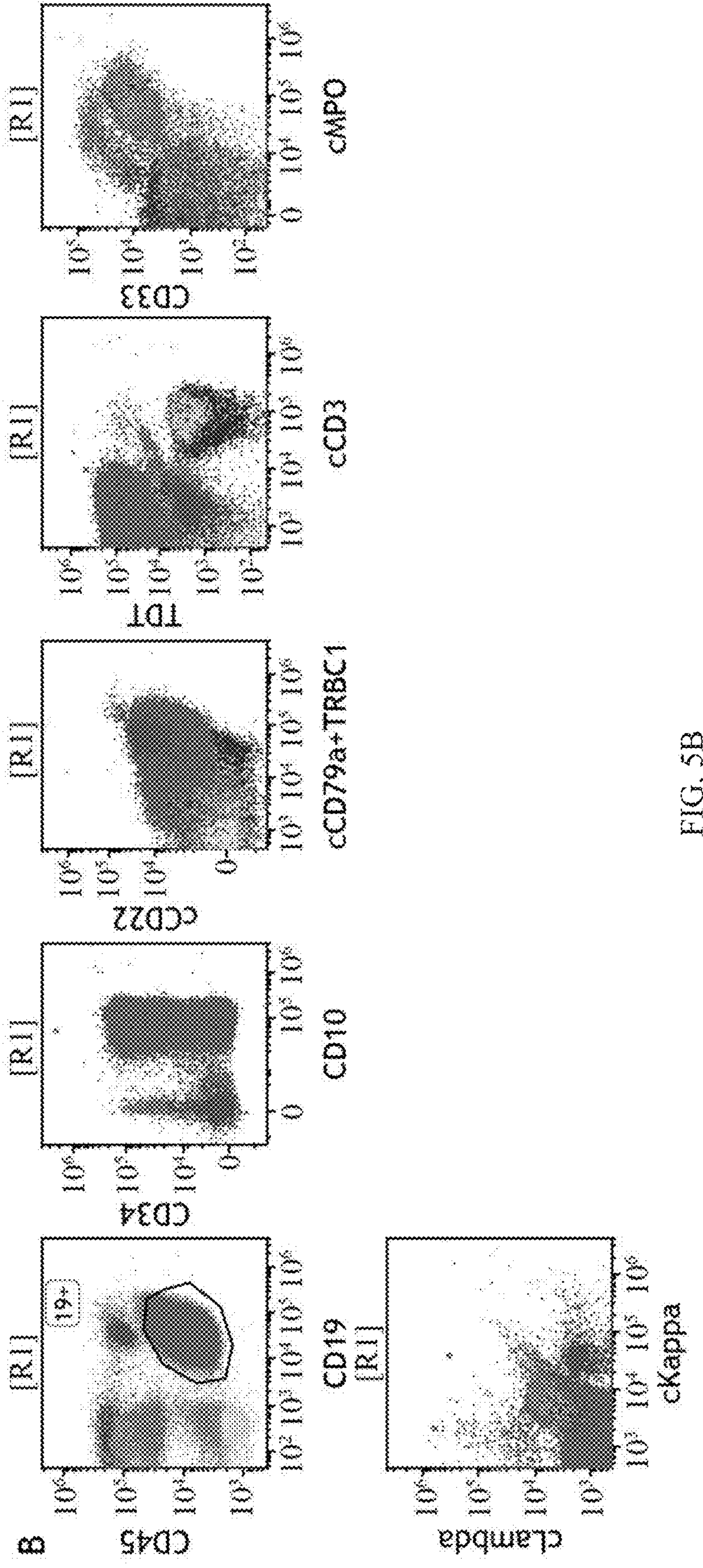

FIG. 5A and FIG. 5B show the test results in a patient with B-ALL/LBL with t (12;21) (p13.2;q22.1); ETV6-RUNX1. FIG. 5A shows the test results for the antibody combination of the present disclosure and FIG. 5B shows the result for the early screening tube. FIG. 5B proves that the immature cells express CD19, nTdT, cCD79a, cCD22 and CD10, partially express CD34, and do not express CD33, ckappa or clambda, which is of the B-ALL-Com subtype. The immature cells do not express cMPO or cCD3, except AML and T-ALL. Furthermore, the antibody combination of the present disclosure was used for B-ALL/LBL genotyping and LAIP judgment. In the CD45/SSC plot of FIG. 5A, the immature cells (immature) account for 75.98%, and the CD19$^{+}$ B cells in the CD45/CD19 plot account for 72.65%. Since the immature cells do not express CD45, and nucleated red blood cells do not express CD45, there is an overlap, and the number of CD19$^{+}$ B cells in the CD45/CD19 plot should prevail. The B cells express CD22, CD24, CD123, CD58$^{dim}$, HLA-DR, CD38$^{dim}$, and CD81$^{dim}$, partially express CD13, and CD25$^{dim}$, and do not express CD20, CD21, CD15, CD66, CD25, CD65, kappa or lambda. Based on the negativity of CD20, CD21, CD66, CD25, CD38$^{dim}$, and CD13, it scores 2 points, and it appears that it is not of the subtype of B-ALL/LBL with BCR/ABL1. Based on the negativity of CD15 and CD65, it appears that it is not of the subtype B-ALL/LBL with t (v;11q23.3). Since no CD66 or CD20 was expressed, it was suspected to be the subtype of B-ALL/LBL with ETV6-RUNX1. LAIP: CD19$^{+}$CD45$^{-}$CD10$^{+}$CD34$^{+}$CD123$^{+}$CD58$^{+}$CD38$^{dim}$. Through gene test, the test result of the patient was ETV6-RUNX1 fusion gene positive, which proved to be B-ALL/LBL with t (12;21) (p13.2;q22.1);ETV6-RUNX1.

Figure 6A:
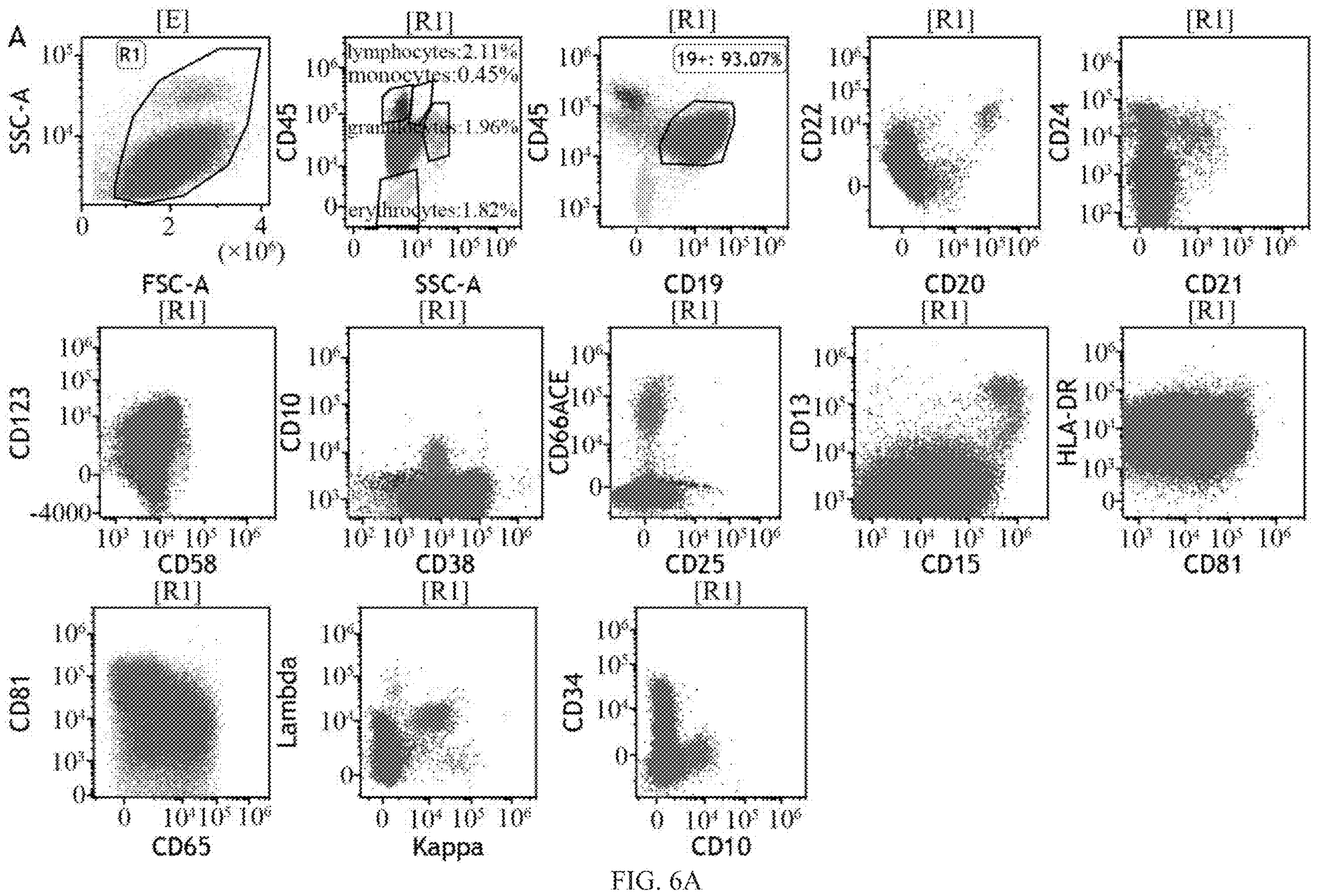
FIG. 6A and FIG. 6B show the test result of a patient with B-ALL/LBL with t (4;11q23.3); KMT2A rearrangement.
Figure 6B:
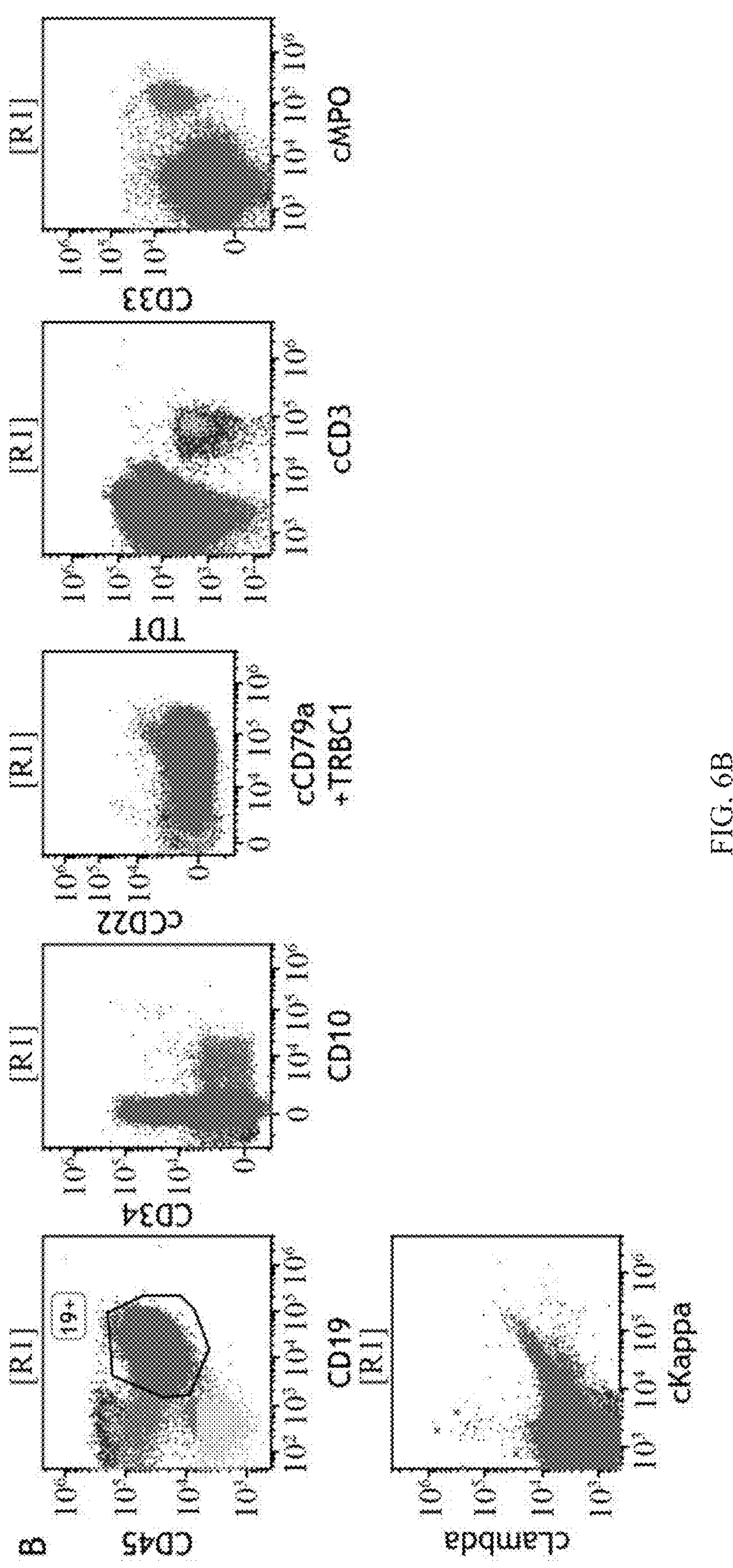

FIG. 6A and FIG. 6B show the test results of a patient with B-ALL/LBL with t (v;11q23.3); KMT2A rearrangement. FIG. 6A is the test results for the antibody combination of the present disclosure, FIG. 6B shows the results for the early screening tube. FIG. 6B proves that the immature cells express CD19, nTdT, and cCD79a, partly express CD34, and do not express CD10, CD33, cCD22, ckappa, or clambda, which is identifies of the B-ALL-Pro subtype. The immature cells do not express cMPO or cCD3, except AML and T-ALL. Furthermore, the antibody combination of the present disclosure was used for B-ALL/LBL genotyping and LAIP judgment. In the CD45/CD19 plot of FIG. 6A, it is shown that CD19+ cells account for 93.07%, CD19+ B cells express CD123, $CD58^{dim}$, CD38, and HLA-DR, partly express CD81, CD15, CD65, and do not express CD22, CD20, CD21, CD24, CD13, CD66, CD10, CD25, kappa or lambda. Based on the Pro subtype and positivity of CD65 and CD15, the subtype of B-ALL/LBL With t (v;11q23.3); KAT2A rearrangement is supported. LAIP:$CD19^{+}CD10^{-}CD34^{+}CD123^{+}CD24^{-}CD38^{+}$. Through gene test, the test result of the patient was KAT2A-AF4 fusion gene positive, which proved to be B-ALL/LBL with t (4;11q23.3);KAT2A rearrangement.

Figure 7A:
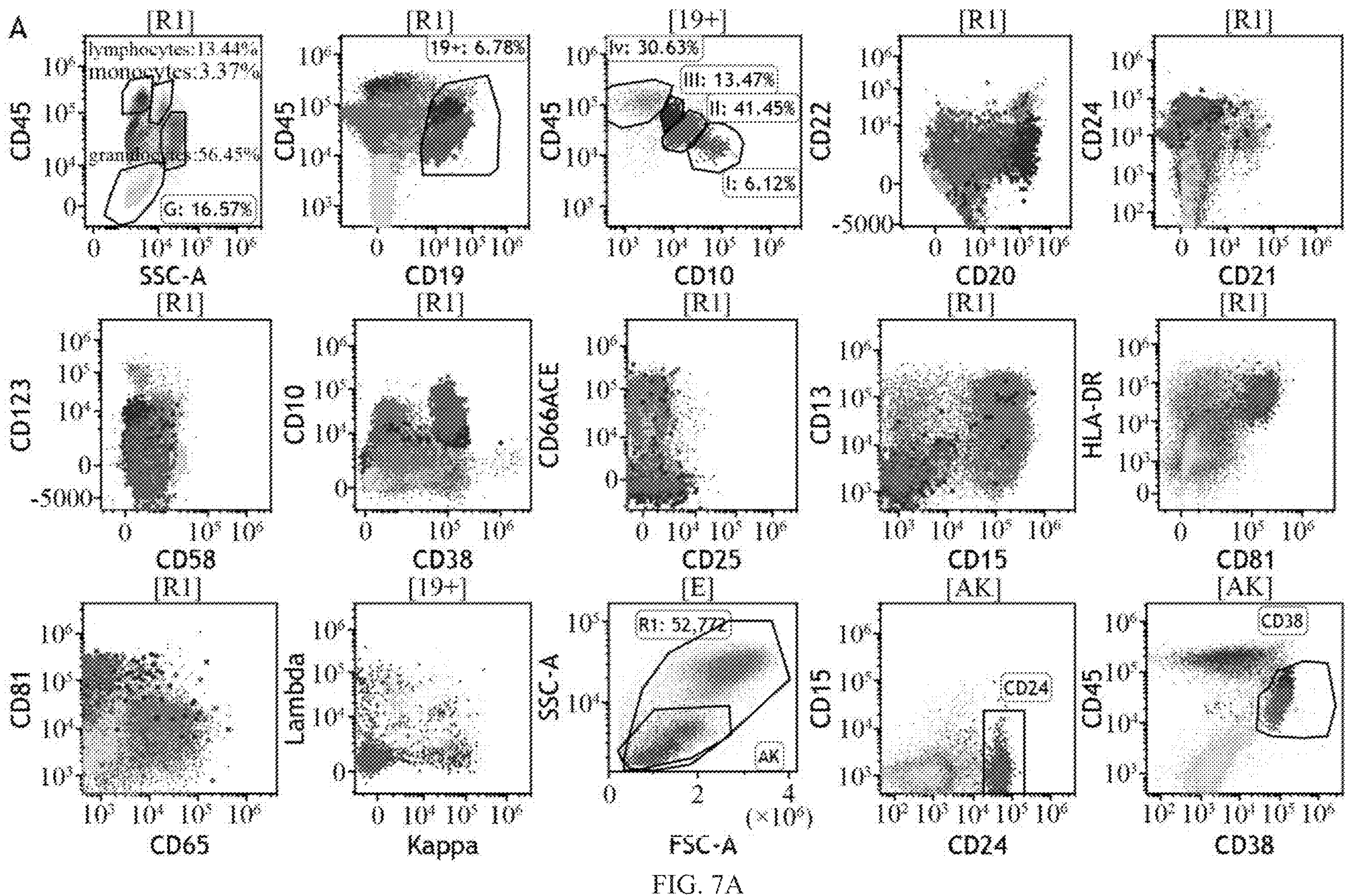
FIG. 7A and FIG. 7B show the expression results of antigens in different differentiation stages of $CD19^+$ B cells in a patient with normal bone marrow.
Figure 7B:
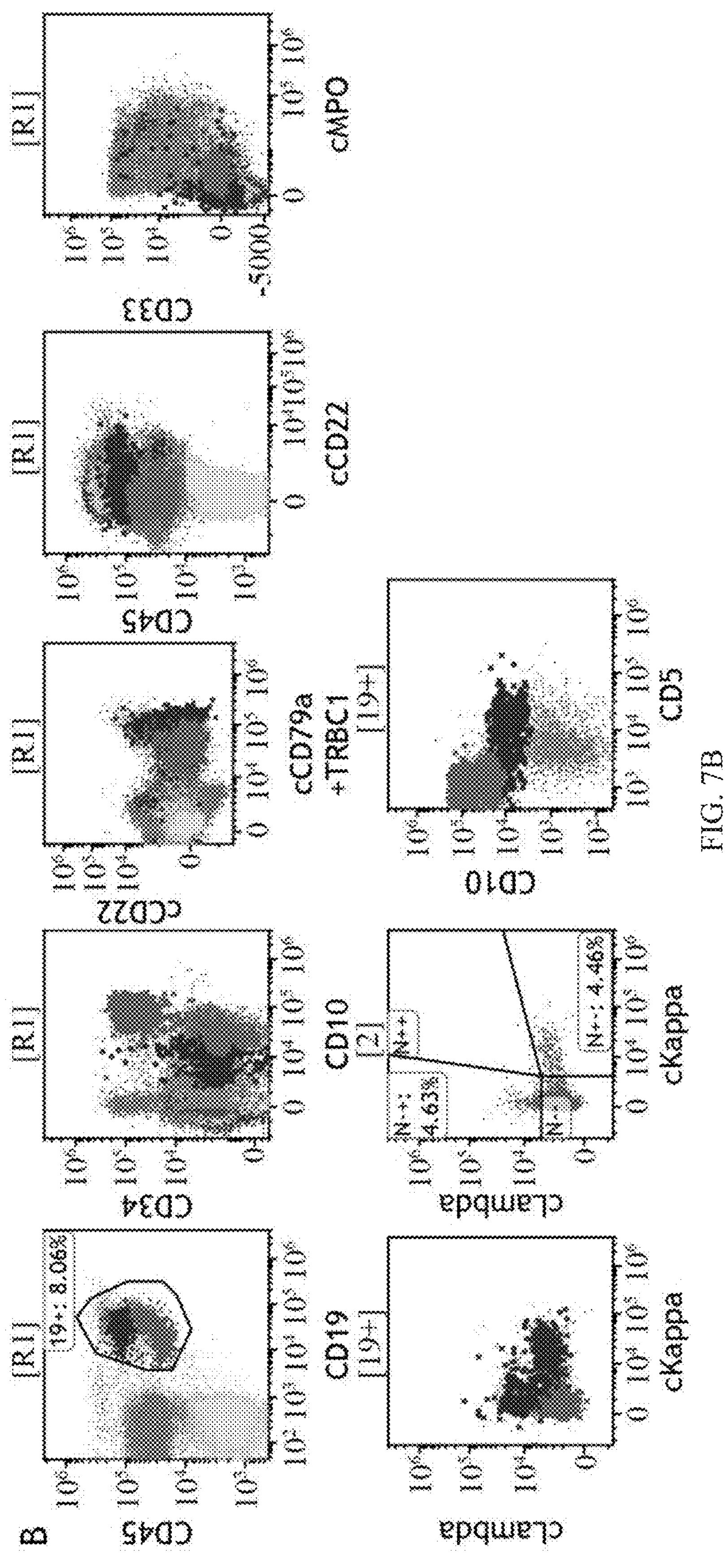

FIG. 7A and FIG. 7B show the results of antigen expression of CD19+ B cells at different differentiation stages in normal bone marrow from a patient. FIG. 7A shows the test results for the antibody combination of the present disclosure and FIG. 7B shows the result for the early screening tube. In the CD45/CD19 plot of FIG. 7A, it is shown that CD19+ cells account for 6.78%, and the CD45/CD10 plot shows the cells within the CD19+ gate. Based on the expression of CD10 and CD45, the B cells are divided into four stages of differentiation from I to IV, wherein I represents the first stage and $CD10^{st+}$ or CD45 is the most weakly expressed. At stages II-IV, the expression of CD10 by B cells is gradually decreased to negative, and the CD45 expression is gradually increased. The gating of CD19+ B cells in FIG. 7B is the same as that in FIG. 7A. By combining the 2 tubes, it can be seen that phase I cells express $CD10^{st}$, $CD45^{dim}$, CD34, nTdT, CD79a, c/mCD22, CD24, $CD58^{dim}$, CD38, HLA-DR, and CD81, and other markers are negative. Stage-II cells express CD10, CD45, CD79a, c/$mCD22^{dim}$, CD24, CD38, HLA-DR, CD81, and CD20, and cKappa/clambda began to be expressed in small amounts, and the rest markers were negative. Stage-III B cells at the near-mature stage express $CD10^{dim}$, $CD45^{st}$, CD79a, c/mCD22, CD24, CD38, HLA-DR, CD81, CD20, c/mKappa and c/mlambda, some cells express CD5 and CD123, and the rest of the markers were negative. Stage IV cells are mature B cells that express $CD45^{st}$, CD79a, c/mCD22, CD20, HLA-DR, c/mKappa, c/mlambda, and $CD21^{+}$ occurred. However, CD10 and CD38 turned negative, CD24 and CD81 turned out to be weakly expressed, and the rest markers of CD34, nTdT, CD123, CD58, and CD5 were all negative. Myeloid-related markers such as CD13, CD15, CD65, CD33, cMPO, and cCD3 were persistently negative.

Figure 8:
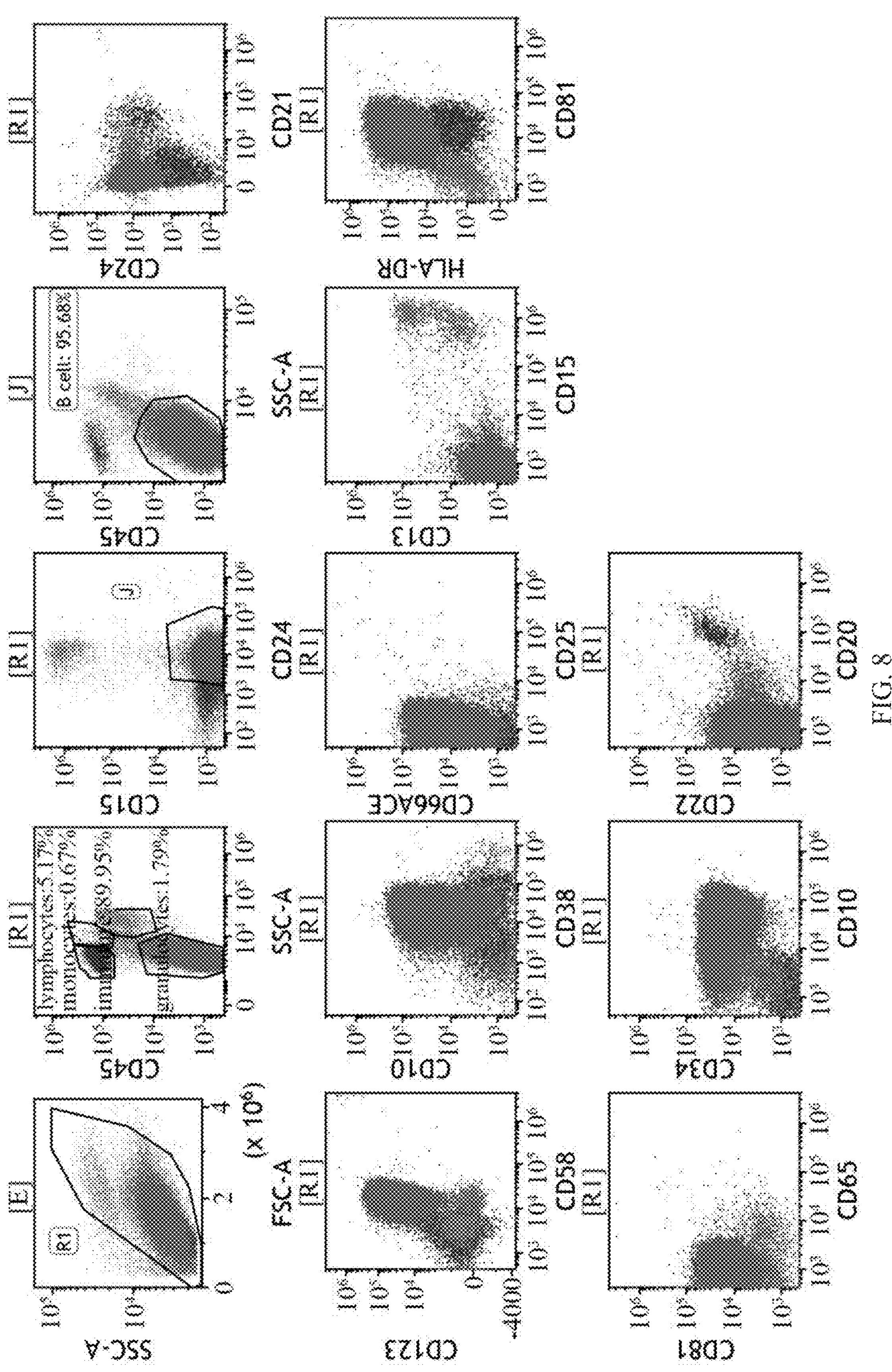
FIG. 8 shows a method for analysis of immune B cells by setting a gate using CD24 in combination with CD15 and CD45/SSC in a patient with $CD24^+$B-ALL/LBL.

FIG. 8 shows a method for analysis of immune B cells by setting a gate using CD24 in combination with CD15 and CD45/SSC in a patient with $CD24^{+}$B-ALL/LBL. At the same time, combined with the results of $CD123^{st+}$, $CD66^{+}$, $CD45^{-}$ and abnormal expression of $CD10^{dim}$, it was considered as LAIP, and it was determined as abnormal immune B cells, which was used for the identification of abnormal leukemia B cells in MRD detection.

Figure 9:
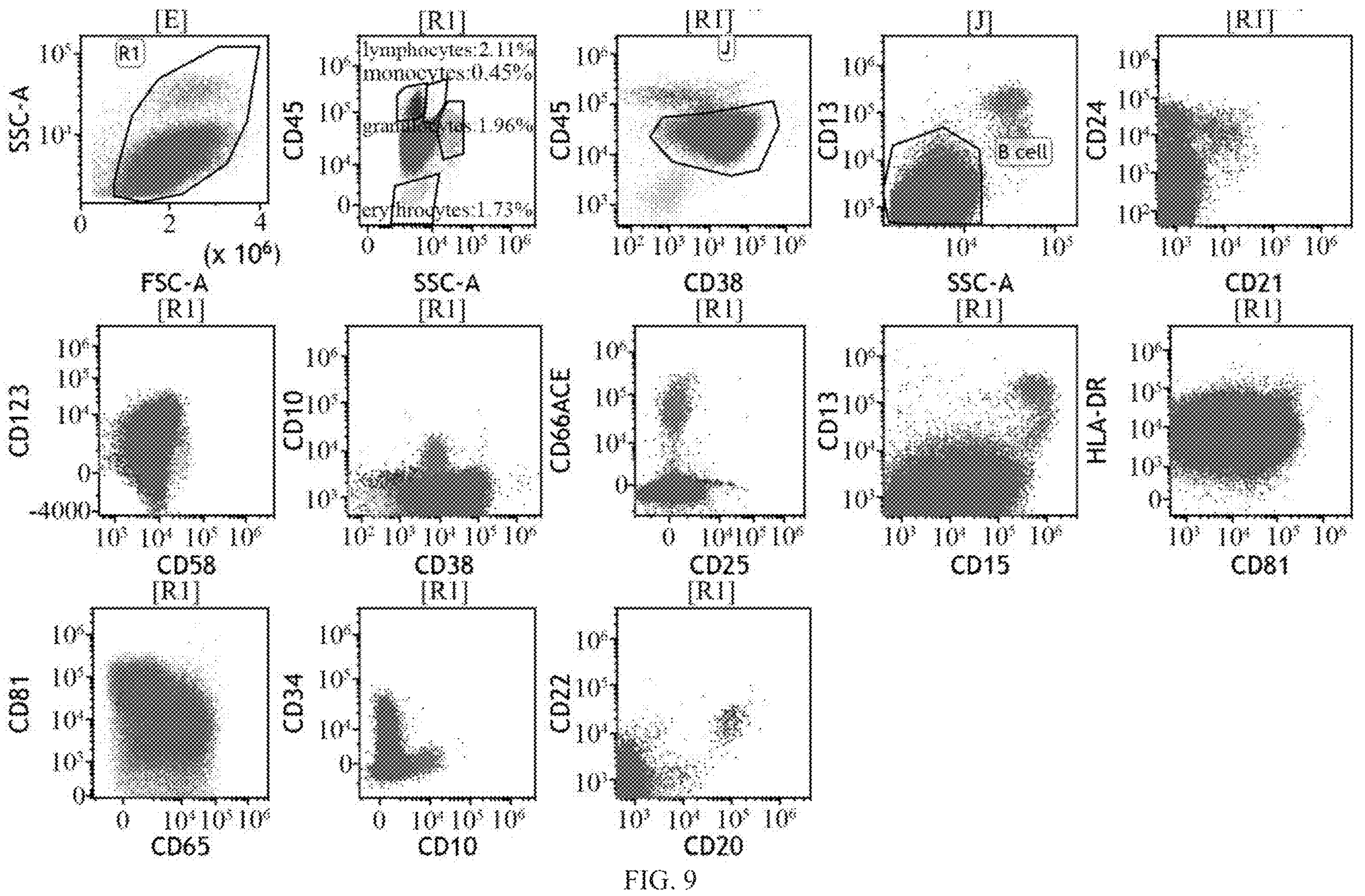
FIG. 9 shows a method for analyzing immune B cells by setting a gate using CD38/CD45, CD13/SSC in a patient with B-ALL/LBL with t (4;11q23.3); KAT2A.

FIG. 9 shows the results for a patient with B-ALL/LBL with t (4;11q23.3); KAT2A patients, since CD24 was hardly expressed in these patients, CD38/CD45, CD13/SSC can be used for the gating analysis of immature B cells. At the same time, by combining with the abnormal expression of $CD10^{-}$, $CD65^{+}$, $CD15^{+}$, and $CD24^{-}$, it can be judged as LAIP. The B cells were determined as abnormal immune B cells and were used for the identification of abnormal leukemia B cells in MRD detection.

Although the present application has been described above in detail with a general description and specific embodiments, it will be apparent to those skilled in the art that some modifications or improvements can be made based on the present disclosure. Therefore, the modifications or improvements without departing from the spirit of the present disclosure should fall within the protection scope of the present disclosure.

What is claimed is:

1. A reagent composition for immunophenotyping and/or MRD monitoring of B lymphoblastic leukemia/lymphoma, wherein the reagent composition consists of a combination of antibodies:

anti-CD22 antibody, anti-CD20 antibody, anti-CD21 antibody, anti-CD45 antibody, anti-CD10 antibody, anti-CD19 antibody, anti-CD24 antibody, anti-CD123 antibody, anti-CD65 antibody, anti-CD15 antibody, anti-CD13 antibody, anti-lambda antibody, anti-HLA-DR antibody, anti-CD34 antibody, anti-CD58 antibody, anti-CD81 antibody, anti-CD66a/c/e antibody, anti-Kappa antibody, anti-CD38 antibody, and anti-CD25 antibody, wherein fluorescein label for anti-CD22 antibody, anti-CD20 antibody, anti-CD21 antibody, anti-CD45 antibody, anti-CD10 antibody, anti-CD19 antibody, anti-CD24 antibody, anti-CD123 antibody, anti-CD65 antibody, anti-CD15 antibody, anti-CD13 antibody, anti-lambda antibody, anti-HLA-DR antibody, anti-CD34 antibody, anti-CD58 antibody, anti-CD81 antibody, anti-CD66a/c/e antibody, anti-Kappa antibody, anti-CD38 antibody, and anti-CD25 antibody are violet-excitable polymer fluorophore, ultraviolet-excitable blue-emitting fluorophore, violet-excitable polymer fluorophore, violet-excitable polymer fluorophore, violet-excitable polymer fluorophore, violet-excitable polymer fluorophore, violet-excitable polymer fluorophore, violet-excitable polymer fluorophore, fluorescein isothiocyanate, green-emitting fluorophore, R-phycoerythrin, R-phycoerythrin-synthetic organic dye tandem dye, R-phycoerythrin-Cyanine5 Tandem dye, Peridinin-chlorophyll-protein complex-Cyanine5.5 tandem dye, Peridinin-chlorophyll-protein complex-synthetic organic dye tandem dye, R-phycoerythrin-Cyanine7 tandem dye, far-red sulfonated coumarin-based fluorophore, red-emitting synthetic organic fluorophore, Allophycocyanin-sulfonated cyanine tandem dye, and Allophycocyanin-sulfonated cyanine tandem dye, respectively.

2. The reagent composition according to claim 1, wherein all of the antibodies are monoclonal antibodies.

3. A method for detecting immunophenotype of B lymphoblastic leukemia/lymphoma and/or MRD monitoring, (a) contacting a biological sample with the reagent composition of claim 1;

(b) acquiring, by a full-spectrum flow cytometer, fluorescence signals from the contacted sample;

(c) analyzing, by software, the signals to obtain 20 antigen-specific parameters; and (d) determining B-ALL/LBL immunophenotype and/or MRD based on the antigen-specific parameters.

4. The method according to claim 3, further comprising:

setting a living cell gate R1, excluding debris and dead cells; setting a lymphocyte gate, a monocyte gate, a granulocyte gate, a nucleated red blood cell gate, and an immature cell gate within gate R1 using CD45/SSC; wherein the immature cells in B lymphoblastic leukemia/lymphoma are immature B cells; when it is not favorable to set a gate for immature B cells in CD45/SSC plot, it will be favorable to set a gate for CD19+ B cells using CD45/CD19 or SSC/CD19, and the latter is used for MRD monitoring; and analyzing the immunophenotype of immune B cells.

5. The method according to claim 4, wherein a gate is set on CD24 and/or CD38 after B lymphoblastic leukemia/lymphoma is treated with CD19-CAR-T and/or CD22-CAR-T.

6. The method according to claim 4, wherein scoring is performed using 6 markers of CD20, CD21, CD38dim, CD66, CD25, and CD13, with each positive antigen being scored as 1 point, and a score of >3 points is to be predicted as BCR/ABL1+ and a score of <3 is to be predicted as BCR/ABL1−.

* * * * *